United States Patent
Kung et al.

(10) Patent No.: US 7,300,944 B2
(45) Date of Patent: *Nov. 27, 2007

(54) PYRAZOLO[3,4-B]PYRIDIN-6-ONES AS GSK-3 INHIBITORS

(75) Inventors: Daniel W. Kung, Salem, CT (US); Travis T. Wager, New London, CT (US)

(73) Assignee: Pfizer Inc., New York, NY (US)

( * ) Notice: Subject to any disclaimer, the term of this patent is extended or adjusted under 35 U.S.C. 154(b) by 486 days.

This patent is subject to a terminal disclaimer.

(21) Appl. No.: 10/875,009

(22) Filed: Jun. 23, 2004

(65) Prior Publication Data

US 2004/0266815 A1    Dec. 30, 2004

Related U.S. Application Data

(60) Provisional application No. 60/483,201, filed on Jun. 27, 2003.

(51) Int. Cl.
*C07D 471/02*    (2006.01)
*A61K 31/4745*   (2006.01)

(52) U.S. Cl. ....................... 514/303; 546/119

(58) Field of Classification Search ................ 546/119; 514/303
See application file for complete search history.

(56) References Cited

U.S. PATENT DOCUMENTS

2002/0103185 A1    8/2002    Sanner et al. .......... 514/217.09

OTHER PUBLICATIONS

Wolff, Manfred E. "Burger's Medicinal Chemistry, 5ed, Part I", John Wiley & Sons, 1995, pp. 975-977.*

Banker (Modern Pharmaceutics) Banker, G.S. et al, "Modern Pharmaceutics, 3ed.", Marcel Dekker, New York, 1996, pp. 451 and 596.*

Quiroga, J. et al., Heterocyclic Comm., vol. 5(2), pp. 115-122, 1999, "Sythesis, Molecular Structure and Tautomerism of 1(2)*H*-Dihidropyrazolo[3,4-b]Pyridin-6-Ones."

Catarzi, D. et al., Arch. Pharm. Pharm. Med. Chem., vol. 300, pp. 383-386, 1997, "Tricyclic Heteroaromatic Systems. Pyrazolo[3,4-*c*]quinolin-4-ones and Pyrazolo[3,4-*c*]quinoline-1,4-diones: Synthesis and Benzodiazepine Receptor Activity."

* cited by examiner

*Primary Examiner*—Zinna N. Davis
(74) *Attorney, Agent, or Firm*—Ye Hua; Stephen D. Prodnuk; Bryan C. Zielinski

(57) ABSTRACT

The present invention provides compounds of formula (I)

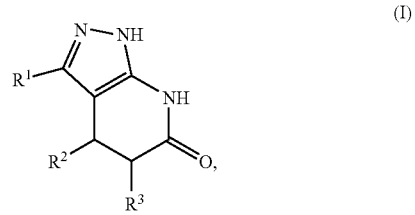

the stereoisomers and prodrugs thereof, and the pharmaceutically acceptable salts of the compounds, stereoisomers, and prodrugs, wherein $R^1$, $R^2$ and $R^3$ are as defined herein; pharmaceutical formulations thereof; and use thereof in the treatment of, inter alia, conditions, diseases, and symptoms such as bipolar disorder, diabetes, dementia, Alzheimer's Disease, stroke, schizophrenia, depression, hair loss, and cancer.

7 Claims, No Drawings

PYRAZOLO[3,4-B]PYRIDIN-6-ONES AS GSK-3 INHIBITORS

This application claims priority to U.S. Provisional Application Ser. No. 60/483,201, filed Jun. 27, 2003.

FIELD OF THE INVENTION

The invention relates to substituted pyrazolo[3,4-b]pyridin-6-ones which are inhibitors of cyclin-dependent protein kinase-2 (cdk-2), cyclin-dependent protein kinase-5 (cdk-5), and glycogen synthase kinase 3 (GSK-3). As such, they are useful in the treatment of, inter alia, conditions, diseases, and symptoms such as bipolar disorder, diabetes, dementia, Alzheimer's Disease, stroke, schizophrenia, depression, hair loss, and cancer.

BACKGROUND OF THE INVENTION

The serine/threonine kinase cdk-2 is essential for normal cellular cycling and plays a critical role in disorders arising from abnormal cell cycling, a common characteristic of many oncological disorders. Inhibitors of cdk-2 are therefore useful in the treatment of various types of cancers and other diseases or conditions related to abnormal cell growth. See, for example, Meijer, et al., Pharmacol. and Therapeutics, 82 (2-3), 279-284 (1999), Sausville, et al., Pharmacol. and Therapeutics, 82 (2-3), 285-292 (1999). The serine/threonine kinase cdk-5, along with its cofactor p25, or the longer cofactor p35, has been linked to neurodegenerative disorders, and inhibitors of cdk-5 are therefore useful in the treatment of disorders such as Alzheimer's Disease, Parkinson's Disease, stroke, and Huntington's Disease. Treatment of such neurodegenerative disorders using cdk-5 inhibitors is supported by the finding that cdk-5 is involved in the phosphorylation of tau protein, and dopamine and cyclic AMP-regulated phosphoprotein (DARPP-32) at threonine 75, and is thus indicated as playing a role in dopaminergic transmission.

Glycogen synthase kinase-3 (GSK-3), a proline-directed, serine/threonine kinase for which two isoforms, GSK-3α and GSK-3β, have been identified, phosphorylates the rate-limiting enzyme of glycogen synthesis, glycogen synthase (GS). See, for example, Embi, et al., Eur. J. Biochem., 107, 519-527 (1980). GSK-3α and GSK-3β are both highly expressed in the body. See, for example, Woodgett, et al., EMBO, 9, 2431-2438 (1990) and Loy, et al., J. Peptide Res., 54, 85-91 (1999). Besides GS, a number of other GSK-3 substrates have been identified, including many metabolic, signaling, and structural proteins. Notable among the plurality of signaling proteins regulated by GSK-3 are many transcription factors, including activator protein-1; cyclic AMP response element binding protein (CREB); the nuclear factor (NF) of activated T-cells; heat shock factor-1; β-catenin; c-Jun; c-Myc; c-Myb; and NF-$_{KB}$. See, for example, C. A. Grimes, et al., Prog. Neurobiol., 65, 391-426 (2001), H. Eldar-Finkelman, Trends in Molecular Medicine, 8, 126-132 (2002), and P. Cohen, et al., Nature, 2, 1-8, (2001). Accordingly, targeting the activity of GSK-3 has significant therapeutic potential in the treatment of many disparate pathologies and conditions, for example, Alzheimer's Disease (A. Castro, et al., Exp. Opin. Ther. Pat., 10, 1519-1527 (2000)); asthma (P. J. Barnes, Ann. Rev. Pharmacol. Toxicol., 42, 81-98 (2002)); cancer (Beals, et al., Science, 275, 1930-1933 (1997), L. Kim, et al., Curr. Opin. Genet. Dev., 10, 508-514 (2000), and Q. Eastman, et al., Curr. Opin. Cell Biol., 11, 233 (1999)); diabetes and its related sequelae, for example, Syndrome X and obesity (S. E. Nikoulina, et al., Diabetes, 51, 2190-2198 (2002), Orena, et al., JBC, 15765-15772 (2000), and Summers, et al., J. Biol. Chem., 274 17934-17940 (1999)); hair loss (S. E. Millar, et al., Dev. Biol., 207, 133-149 (1999) and E. Fuchs, et al., Dev. Cell, 1, 13-25 (2001)); inflammation (P. Cohen, Eur. J. Biochem., 268, 5001-5010 (2001)); mood disorders, such as depression (A. Adnan, et al., Chem. Rev., 101, 2527-2540 (2001) and R. S. B. Williams, et al., Trends Phamacol. Sci., 21, 61-64 (2000)); neuronal cell death and stroke (D. A. E. Cross, et al., J. Neurochem., 77, 94-102 (2001) and C. Sasaki, et al., Neurol. Res., 23, 588-592 (2001)); bipolar disorder (Klein, et al., PNAS, 93, 8455-8459 (1996)); skeletal muscle atrophy (G. J. Brunn, et al., Science, 277, 99-101 (1997), R. E. Rhoads, J. Biol. Chem., 274, 30337-30340 (1999), V. R. Dharmesh, et al., Am. J. Physiol. Cell Physiol. 283, C545-551 (2002), and K. Baar, et al., A. J. Physiol., 276, C120-C127 (1999)); decreased sperm motility (Vijayaraghavan, et al., Biol. Reproduction, 54, 709-718 (1996)); and in cardio-protection (C. Badorff, et al., J. Clin. Invest., 109, 373-381 (2002), S. Haq, et al., J. Cell Biol., 151, 117-129 (2000), and H. Tong, et al., Circulation Res., 90, 377-379 (2002)).

SUMMARY OF THE INVENTION

The present invention provides compounds of formula (I)

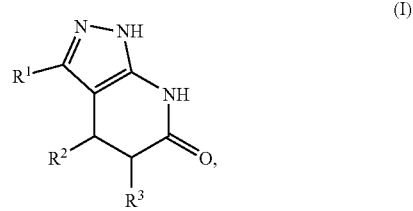

the stereoisomers and prodrugs thereof, and the pharmaceutically acceptable salts of the compounds, stereoisomers, and prodrugs, wherein $R^1$, $R^2$ and $R^3$ are as defined herein; pharmaceutical formulations thereof; and use thereof in the treatment of, inter alia, conditions, diseases, and symptoms such as bipolar disorder, diabetes, dementia, Alzheimer's Disease, stroke, schizophrenia, depression, hair loss, and cancer.

DETAILED DESCRIPTION OF THE INVENTION

The present invention relates to compounds of formula (I)

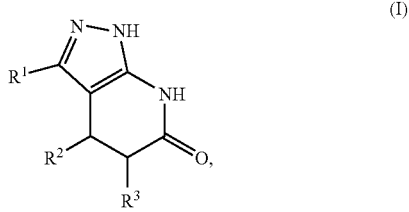

the stereoisomers and prodrugs thereof, and the pharmaceutically acceptable salts of the compounds, stereoisomers, and prodrugs, wherein:

R¹ and R² are, independently, hydrogen; —(C₁-C₈)alkyl; —(C₁-C₈)alkoxy; —(C₃-C₁₁)cycloalkyl; heterocycloalkyl; aryl; or heteroaryl; and R³ is hydrogen; —(C₁-C₈)alkyl; —(C₁-C₈)alkoxy; or —(C₃-C₁₁)cycloalkyl;

wherein each R¹, R², and R³ is optionally, and independently, substituted with from one to six of: (A) halogen; (B) aryl, optionally substituted with from one to three of: (i) —OH; (ii) —CN; (iii) halogen; (iv) heteroaryl; (v) —CH₂OR⁴; or (vi) —CH₂NR⁴R⁵; (C) heteroaryl; (D) —NO₂; (E) —CN; (F) —(C₁-C₈)alkyl, optionally substituted with from one to three halogen atoms; (G) —(C₁-C₈)thioalkoxy; (H) —NR⁴R⁵; (I) —NR⁴C(=O)R⁵; (J) —NR⁴C(=O)NR⁴R⁵; (K) —NR⁴(SO₂)R⁵; (L) —NR⁴(SO₂)NR⁴R⁵; (M) —OR⁴; (N) —OC(=O)R⁴; (O) —OC(=O)OR⁴; (P) —C(=O)OR⁴; (Q) —C(=O)R⁴; (R) —C(=O)NR⁴R⁵; (S) —OC(=O)NR⁴R⁵; (T) —OC(=O)SR⁴; (U) —SR⁴; (V) —S(=O)R⁴; (W) —SO₂R⁴; or (X) —SO₂R⁴R⁵; wherein:

R⁴ and R⁵ are, independently, hydrogen; aryl, optionally substituted with from one to three of: halogen; —OH; —(C₁-C₈)alkyl, optionally substituted with aryl; or —(C₃-C₁₁)cycloalkyl;

provided that when R¹ is

wherein X is hydrogen, —CH₃, —OCH₃, Cl, Br, or —NO₂, and R² is

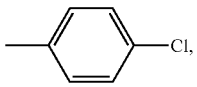

then R³ is not hydrogen.

A generally preferred subgroup of the compounds of formula (I) comprises those compounds wherein:

R¹ is —(C₁-C₅)alkyl or —(C₃-C₆)cycloalkyl;

R² is hydrogen; —(C₁-C₈)alkyl; —(C₁-C₈)alkoxy; —(C₃-C₉)cycloalkyl; heterocycloalkyl; aryl; or heteroaryl; and R³ is hydrogen; —(C₁-C₃)alkyl; —(C₁-C₆)alkoxy; or —(C₃-C₆)cycloalkyl;

wherein each R¹, R², and R³ is optionally, and independently, substituted with from one to six of: (A) halogen; (B) aryl, optionally substituted with from one to three of: (i) —OH; (ii) —CN; (iii) halogen; (iv) heteroaryl; (v) —CH₂OR⁴; or (vi) —CH₂NR⁴R⁵; (C) heteroaryl; (D) —NO₂; (E) —CN; (F) —(C₁-C₈)alkyl, optionally substituted with from one to three fluorine atoms; (G) —(C₁-C₈)thioalkoxy; (H) —NR⁴R⁵; (I) —NR⁴C(=O)R⁵; (J) —NR⁴C(=O)NR⁴R⁵; (K) —NR⁴(SO₂)R⁵; (L) —NR⁴(SO₂)NR⁴R⁵; (M) —OR⁴; (N) —OC(=O)R⁴; (O) —OC(=O)OR⁴; (P) —C(=O)OR⁴; (Q) —C(=O)R⁴; (R) —C(=O)NR⁴R⁵; (S) —OC(=O)NR⁴R⁵; (T) —OC(=O)SR⁴; (U) —SR⁴; (V) —S(=O)R⁴; (W) —SO₂R⁴; or (X) —SO₂R⁴R⁵.

Another generally preferred subgroup of the compounds of formula (I) comprises those compounds wherein:

R¹ is —(C₁-C₅)alkyl or —(C₃-C₆)cycloalkyl;

R² is hydrogen; —(C₁-C₈)alkyl; —(C₁-C₈)alkoxy; —(C₃-C₉)cycloalkyl; heterocycloalkyl; aryl; or heteroaryl; and R³ is hydrogen;

wherein each R¹ or R² is optionally, and independently, substituted with from one to six of: (A) Cl or Fl; (B) aryl, optionally substituted with from one to three of: (i) —OH; (ii) —CN; (iii) halogen; (iv) heteroaryl; (v) —CH₂OR⁴; or (vi) —CH₂NR⁴R⁵; (C) heteroaryl; (E) —CN; (F) —CF₃; (G) —(C₁-C₈)thioalkoxy; (H) —NR⁴R⁵; (I) —NR⁴C(=O)R⁵; (J) —NR⁴C(=O)NR⁴R⁵; (K) —NR⁴(SO₂)R⁵; (L) —NR⁴(SO₂)NR⁴R⁵; (M) —OR⁴; (N) —OC(=O)R⁴; (O) —OC(=O)OR⁴; (P) —C(=O)OR⁴; (Q) —C(=O)R⁴; (R) —C(=O)NR⁴R⁵; (S) —OC(=O)NR⁴R⁵; (T) —OC(=O)SR⁴; (W) —SO₂R⁴; or (X) —SO₂R⁴R⁵.

The compounds and intermediates of the present invention may be named according to either the IUPAC (International Union for Pure and Applied Chemistry) or CAS (Chemical Abstracts Service, Columbus, Ohio) nomenclature systems.

The carbon atom content of the various hydrocarbon-containing moieties may be indicated by a prefix designating the minimum and maximum number of carbon atoms in the moiety, i.e., the prefix (Cₐ-Cᵦ)alkyl indicates an alkyl moiety of the integer "a" to "b" carbon atoms, inclusive. Thus, for example, "(C₁-C₆)alkyl" refers to an alkyl group of one to six carbon atoms inclusive, for example, methyl, ethyl, propyl, isopropyl, butyl, isobutyl, pentyl, isopentyl, hexyl, and the like, including all regioisomeric forms thereof, and straight and branched chain forms thereof.

The term "alkoxy" refers to straight or branched, monovalent, saturated aliphatic chains of carbon atoms bonded to an oxygen atom, wherein the alkoxy group optionally incorporates one or more double or triple bonds, or a combination of double bonds and triple bonds. Examples of alkoxy groups include methoxy, ethoxy, propoxy, butoxy, iso-butoxy, tert-butoxy, and the like.

The term "alkyl" refers to straight, or branched, monovalent chains of carbon atoms, wherein the alkyl group optionally incorporates one or more double or triple bonds, or a combination of double bonds and triple bonds. Examples of alkyl groups include methyl, ethyl, propyl, isopropyl, butyl, isobutyl, vinyl, allyl, 2-methylpropenyl, 2-butenyl, 1,3-butadienyl, ethynyl, propargyl, 2-butynyl, and the like.

The term "aryl" denotes a cyclic, aromatic hydrocarbon. Examples of aryl groups include anthracenyl, fluorenyl, phenanthrenyl, phenyl, naphthyl, and the like.

The term "cycloalkyl" denotes a saturated monocyclic, or polycyclic, cycloalkyl group, optionally fused to an aryl group, wherein the cycloalkyl group optionally incorporates one or more double or triple bonds, or a combination of double bonds and triple bonds, but which is not aromatic. Examples of cycloalkyl groups include adamantanyl, cyclopropyl, cyclobutyl, cyclopentyl, cyclohexyl, cycloheptyl, decahydronaphthalinyl, norbornanyl, and the like.

The term "halogen" represents chloro, fluoro, bromo, and iodo.

The term "heteroaryl" denotes a monocyclic, or polycyclic, aromatic hydrocarbon group wherein one or more carbon atoms have been replaced with heteroatoms selected from the group consisting of nitrogen, oxygen, and sulfur. If the heteroaryl group contains more than one heteroatom, the heteroatoms may be the same or different. Examples of heteroaryl groups include benzofuranyl, benzothienyl, benzimidazolyl, benzoxazolyl, benzothiazolyl, chromenyl, furyl, imidazolyl, indazolyl, indolizinyl, indolyl, isobenzofuranyl, isoindolyl, isoquinolyl, isothiazolyl, isoxazolyl, naphthyridinyl, oxadiazolyl, oxazinyl, oxazolyl, phthalazinyl, pteridinyl, purinyl, pyranyl, pyrazinyl, pyrazolyl, pyridazinyl, pyrido[3,4-b]indolyl, pyridyl, pyrimidyl, pyrrolyl, quinolizinyl, quinolyl, quinoxalinyl, thiadiazolyl, thiatriazolyl, thiazolyl, thienyl, triazinyl, triazolyl, xanthenyl, and the like.

The term "heterocycloalkyl" denotes a saturated monocyclic, or polycyclic, cycloalkyl group, optionally fused to an aromatic or heteroaromatic hydrocarbon group, in which at least one of the carbon atoms has been replaced with a heteroatom selected from the group consisting of nitrogen, oxygen, and sulfur. If the heterocycloalkyl group contains more than one heteroatom, the heteroatoms may be the same or different. Examples of such heterocycloalkyl groups include azabicycloheptanyl, azetidinyl, benzazepinyl, 1,3-dihydroisoindolyl, dioxanyl, carbazolyl, dioxolanyl, dithianyl, indolinyl, imidazolidinyl, morpholinyl, quinuclidinyl, phenoxazinyl, piperazinyl, piperidyl, pyrazolidinyl, pyrrolidinyl, tetrahydrofuryl, tetrahydroindolyl, tetrahydroisoquinolinyl, tetrahydropyranyl, tetrahydroquinolinyl, tetrahydroquinoxalinyl, tetrahydrothiopyranyl, tetrahydro-2H-1,4-thiazinyl, thiazolidinyl, thiomorpholinyl, thioxanthenyl, thioxanyl, trithianyl, and the like.

The term "thioalkoxy" denotes an alkoxy group, as defined hereinabove, wherein a sulfur atom has been substituted for the oxygen atom.

A cyclic group may be bonded to another group in more than one way. If no particular bonding arrangement is specified, then all possible arrangements are intended. For example, the term "pyridyl" includes 2-, 3-, or 4-pyridyl, and the term "thienyl" includes 2- or 3-thienyl.

The phrase "pharmaceutically acceptable" indicates that the designated carrier, vehicle, diluent, excipient(s), and/or salt must be chemically and/or physically compatible with the other ingredients comprising the formulation, and physiologically compatible with the recipient thereof.

The term "prodrug" refers to a compound that is a drug precursor which, following administration, releases the drug in vivo via a chemical or physiological process (e.g., upon being brought to physiological pH or through enzyme activity). A discussion of the preparation and use of prodrugs is provided by T. Higuchi and W. Stella, "Prodrugs as Novel Delivery Systems, Vol. 14 of the ACS Symposium Series, and in Bioreverible Carriers in Drug Design, ed. Edward B. Roche, American Pharmaceutical Association and Pergamon Press, 1987.

The term "radical" denotes a group of atoms that behaves as a single atom in a chemical reaction, e. g., an organic radical is a group of atoms that imparts characteristic properties to a compound containing it, or which remains unchanged during a series of reactions, or transformations.

The term "salts" refers to organic and inorganic salts of a compound of formula (I), or a stereoisomer, or prodrug thereof. These salts can be prepared in situ during the final isolation and purification of a compound, or by separately reacting a compound of formula (I), or a stereoisomer or prodrug thereof, with a suitable organic or inorganic acid or base and isolating the salt thus formed. Representative salts include, but are not limited to, the hydrobromide, hydrochloride, sulfate, bisulfate, nitrate, acetate, oxalate, besylate, palmitate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. These may also include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. For additional examples see, for example, Berge, et al., J. Pharm. Sci., 66, 1-19 (1977).

The term "substituted" means that a hydrogen atom on a molecule has been replaced with a different atom or molecule. The atom or molecule replacing the hydrogen atom is denoted as a "substituent."

The symbol "—" represents a covalent bond.

The phrase "reaction-inert solvent" or "inert solvent" refers to a solvent, or mixture of solvents, that does not interact with starting materials, reagents, intermediates, or products in a manner that adversely affects their desired properties.

The terms "treating", "treated", or "treatment" as employed herein includes preventative (e.g., prophylactic), palliative, or curative use or result.

The compounds of formula (I) may contain asymmetric or chiral centers and, therefore, exist in different stereoisomeric forms. It is intended that all stereoisomeric forms of the compounds of formula (I) as well as mixtures thereof, including racemic mixtures, form part of the present invention. In addition, the present invention embraces all geometric and positional isomers. For example, if a compound of formula (I) incorporates a double bond, both the cis- and trans-forms, as well as mixtures thereof, are embraced within the scope of the invention.

Diastereomeric mixtures can be separated into their individual diastereomers on the basis of their physical chemical differences by methods well-known to those of ordinary skill in the art, such as by chromatography and/or fractional crystallization. Enantiomers can be separated by converting the enantiomeric mixture into a diastereomeric mixture by reaction with an appropriate optically active compound (e.g., alcohol), separating the diastereomers and converting (e.g., hydrolyzing) the individual diastereomers to the corresponding pure enantiomers. Also, some of the compounds of formula (I) may be atropisomers (e.g., substituted biaryls) and are also considered as part of the invention.

The compounds of formula (I) may exist in unsolvated as well as solvated forms with pharmaceutically acceptable solvents, such as water, ethanol, and the like, and it is intended that the invention embrace both solvated and unsolvated forms.

The compounds of formula (I) may exist as tautomeric mixtures in equilibrium, represented hereinbelow by structural formulae (I) and (Ia). Although, for illustrative convenience, the compounds of the present invention are depicted as comprising the single tautomer (I), both tautomeric forms (I) and (Ia) are embraced within the scope of the invention.

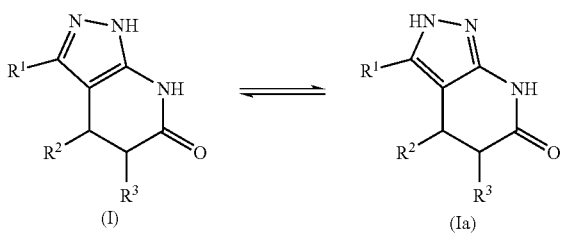

The present invention also embraces isotopically-labeled compounds of formula (I), which are identical to those recited herein, but for the fact that one or more atoms are replaced by an atom having an atomic mass or mass number different from the atomic mass or mass number usually found in nature. Examples of isotopes that can be incorporated into compounds of formula (I) include isotopes of hydrogen, carbon, nitrogen, oxygen, phosphorus, fluorine, and chlorine, such as $^2H$, $^3H$, $^{13}C$, $^{14}C$, $^{15}N$, $^{18}O$, $^{17}O$, $^{31}P$, 32P, 35S, $^{18}F$, and $^{36}Cl$, respectively. The compounds of formula (I), the stereoisomers and prodrugs thereof, and the pharmaceutically acceptable salts of the compounds, stereoisomers, or prodrugs, that contain the aforementioned isotopes and/or other isotopes of the other atoms are intended to be within the scope of the instant invention.

Certain isotopically-labeled compounds of formula (I), for example those compounds into which radioactive isotopes such as $^3H$ and $^{14}C$ are incorporated, are useful in compound and/or substrate tissue distribution assays. Tritiated, i.e., $^3H$, and carbon-14, i.e., $^{14}C$, isotopes are particularly preferred for their relative ease of preparation and facile detection. Furthermore, substitution with heavier isotopes such as deuterium, i.e., $^2H$, may afford certain therapeutic advantages resulting from greater metabolic stability, for example, increased in vivo half-life, or reduced dosage requirements and, hence, may be preferred in some circumstances. The isotopically-labeled compounds of formula (I) can generally be prepared by carrying out procedures analogous to those disclosed in the Scheme and/or Examples set forth hereinbelow, by substituting an isotopically-labeled reagent for a non-isotopically-labeled reagent.

In another aspect, the invention provides methods of treating glycogen synthase kinase-3-mediated conditions, diseases, or symptoms in a mammal in need of such treatment which methods comprise administering to a mammal in need of such treatment a therapeutically effective amount of a compound of formula (I), a stereoisomer or prodrug thereof, or a pharmaceutically acceptable salt of the compound, stereoisomer, or prodrug; a pharmaceutical composition comprising a compound of formula (I), a stereoisomer or prodrug thereof, or a pharmaceutically acceptable salt of the compound, stereoisomer, or prodrug, and a pharmaceutically acceptable carrier, vehicle, or diluent; or a combination of an amount of a compound of formula (I), a stereoisomer or prodrug thereof, or a pharmaceutically acceptable salt of the compound, stereoisomer, or prodrug, and an amount of one or more of: (i) an anti-angiogenesis agent, (ii) a signal transduction inhibitor, (iii) an anti-proliferative agent, (iv) an NK-1 receptor antagonist, (v) a $5HT_{1D}$ receptor antagonist, (vi) a selective serotonin reuptake inhibitor (SSRI), (vii) an anti-psychotic agent, (viii) an acetylcholinesterase inhibitor, (ix) a neuroprotectant, (x) tissue plasminogen activator (TPA), (xi) neutrophil inhibitory factor (NIF), and (xii) a potassium channel modulator; or a pharmaceutical composition comprising the aforementioned combinations.

Preferred conditions, diseases, and symptoms treatable according to the instant methods are those selected from the group consisting of Alzheimer's Disease, asthma, atherosclerosis, anxiety, bipolar disorder, cancer, diabetes, dementia, depression, frailty, hair loss, heart failure, essential hypertension, hyperglycemia, hyperlipidemia, hypoglycemia, inflammation, ischemia, male fertility and sperm motility, mood disorders, neuronal cell death, obesity, obsessive compulsive disorder, polycystic ovary disorder, schizophrenia, stroke, Syndrome X, and traumatic brain injury.

Frailty is characterized by the progressive and relentless loss of skeletal muscle mass resulting in a high risk of injury from fall, difficulty in recovery from illness, prolongation of hospitalization, and long-term disability requiring assistance in daily living. The reduction of muscle mass and physical strength typically leads to diminished quality of life, loss of independence, and mortality. Frailty is normally associated with aging, but may also result when muscle loss and reduced strength occur due to other factors, such as disease-induced cachexia, immobilization, or drug-induced sarcopenia. Another term that has been used to denote frailty is sarcopenia, which is a generic term for the loss of skeletal muscle mass, or quality. Examples of skeletal muscle properties that contribute to its overall quality include contractility, fiber size and type, fatiguability, hormone responsiveness, glucose uptake/metabolism, and capillary density.

Generally preferred anti-angiogenesis agents may comprise, for example, matrix metalloproteinase-2 (MMP-2) inhibitors, matrix metalloproteinase-9 (MMP-9) inhibitors, and cyclooxygenase-II (COX-II) inhibitors. Examples of useful MMP-2 and MMP-9 inhibitors are disclosed in, for example, PCT International Application Publication Nos. WO 98/34915 and WO 98/34918, and U.S. Pat. Nos. 5,240,958; 5,310,763; 5,455,258; 5,506,242; 5,530,161; 5,552,419; 5,672,615; 5,861,510; 5,863,949; 5,932,595; 5,994,351; 6,077,864; 6,087,392; 6,090,852; 6,110,964; 6,147,061; 6,147,074; 6,303,636; 6,380,219; and 6,387,931. Examples of COX-II inhibitors useful in the present combinations and methods comprise CELEBREX® (celecoxib, U.S. Pat. No. 5,466,823), valdecoxib (U.S. Pat. No. 5,633,272), and rofecoxib (U.S. Pat. No. 5,474,995). Generally preferred MMP-2 and MMP-9 inhibitors are those that exhibit little or no activity inhibiting MMP-1. Especially preferred MMP-2 and MMP-9 inhibitors are those that selectively inhibit MMP-2 and/or MMP-9 relative to other MMP inhibitors, i.e., MMP-1, MMP-3, MMP-4, MMP-5, MMP-6, MMP-7, MMP-8, MMP-10, MMP-11, MMP-12, and MMP-13. Specific examples of MMP inhibitors useful in the present combinations and methods comprise AG-3340, RO 32-3555, RS 13-0830, and the following compounds:

3-[[4-(4-fluoro-phenoxy)-benzenesulfonyl]-(1-hydroxycarbamoyl-cyclopentyl)-amino]-propionic acid;

3-exo-3-[4-(4-fluoro-phenoxy)-benzenesulfonyl-amino]-8-oxa-bicyclo[3.2.1]octane-3-carboxylic acid hydroxyamide;

(2R, 3R) 1-[4-(2-chloro-4-fluoro-benzyloxy)-benzenesulfonyl]-3-hydroxy-3-methyl-piperidine-2-carboxylic acid hydroxyamide;

4-[4-(4-fluoro-phenoxy)-benzenesulfonyl-amino]-tetrahydro-pyran-4-carboxlyic acid hydroxyamide;

3-[[4-(4-fluoro-phenoxy)-benzenesulfonyl]-(1-hydroxycarbamoyl-cyclobutyl)-amino]-propionic acid;

4-[4-(4-chloro-phenoxy)-benzenesulfonyl-amino]-tetrahydro-pyran-4-carboxlyic acid hydroxyamide;

(R)-3-[4-(4-chloro-phenoxy)-benzenesulfonyl-amino]-tetrahydro-pyran-3-carboxlyic acid hydroxyamide;

(2R,3R) 1-[4-(4-fluoro-2-methyl-benzyloxy)-benzenesulfonyl]-3-hydroxy-3-methyl-piperidine-2-carboxylic acid hydroxyamide;

3-[[4-(4-fluoro-phenoxy)-benzenesulfonyl]-(1-hydroxycarbamoyl-1-methyl-ethyl)-amino]-propionic acid;

3-[[4-(4-fluoro-phenoxy)-benzenesulfonyl]-(4-hydroxycarbamoyl-tetrahydro-pyran-4-yl)-amino]-propionic acid;

3-exo-3-[4-(4-chloro-phenoxy)-benzenesulfonyl-amino]-8-oxa-bicyclo[3.2.1]octane-3-carboxylic acid hydroxyamide;

3-endo-3-[4-(4-fluoro-phenoxy)-benzenesulfonyl-amino]-8-oxa-bicyclo[3.2.1]octane-3-carboxylic acid hydroxyamide; and (R)-3-[4-(4-fluoro-phenoxy)-benzenesulfonyl-amino]-tetrahydro-furan-3-carboxylic acid hydroxyamide; and the pharmaceutically acceptable salts and solvates thereof.

Generally preferred signal transduction inhibitors may comprise, for example, epidermal growth factor receptor (EGFR) response inhibitors, such as EGFR antibodies, EGF antibodies, and molecules that are EGFR inhibitors; vascular endothelial growth factor (VEGF) inhibitors; and erbB2 receptor inhibitors, such as molecules or antibodies that bind to the erbB2 receptor, for example, HERCEPTIN® (Genentech Inc.; South San Francisco, Calif.). EGFR inhibitors are described in, for example, PCT International Application Publication No. WO 98/14451, and U.S. Pat. Nos. 5,679,683; 5,747,498; and 6,391,874. EGFR-inhibiting agents may comprise, for example, the monoclonal antibodies C225 and anti-EGFR 22Mab (Imclone Systems, Inc.), ZD-1839, BIBX-1382, MDX-103, VRCTC-310, and EGF fusion toxin (Seragen Inc.; Hopkinton, Mass.). VEGF inhibitors are disclosed in, for example, PCT International Application Publication No. WO 99/24440, and U.S. Pat. Nos. 5,792,783; 5,834,504; 5,851,999; 5,883,113; 5,886,020; 6,051,593; 6,114,371; 6,133,305; 6,162,804; 6,174,889; 6,207,669; 6,235,741; 6,291,455; 6,294,532; 6,310,238; 6,380,203; and 6,395,734. Specific VEGF inhibitors may comprise, for example, Su-5416, IM862, anti-VEGF monoclonal antibody (Cytran Inc.; Kirkland, Wash.), and angiozyme (Ribozyme; Boulder, Colo.). ErbB2 receptor inhibitors are disclosed in, for example, PCT International Application Publication Nos. WO 97/13760, WO 99/35132, and WO 99/35146, and U.S. Pat. Nos. 5,679,683; 5,587,458; 5,877,305; 6,207,669; and 6,391,874. Specific erbB2 receptor inhibitors may comprise, for example, GW-282974 (Glaxo Wellcome plc.), and the monoclonal antibody AR-209 (Aronex Pharmaceuticals Inc.; The Woodlands, Tex.).

Generally preferred anti-proliferative agents may comprise, for example, cytotoxic lymphocyte antigen 4 (CTLA4) antibodies, and other agents capable of blocking CTLA4; and farnesyl transferase inhibitors.

Examples of NK-1 receptor antagonists are disclosed in, for example, U.S. Pat. Nos. 5,122,525; 5,162,339; 5,232,929; 5,332,817; 5,703,240; 5,716,965; 5,719,147; 5,744,480; 5,763,699; 5,773,450; 5,807,867; 5,843,966; 5,852,038; 5,886,009; and 5,939,433.

Examples of 5HT1$_D$ receptor antagonists useful in the present combinations and methods are disclosed in, for example, PCT International Application Publication No. WO 94/21619, and U.S. Pat. Nos. 5,358,948; 5,510,350; 6,380,186; 6,403,592; 6,423,708; and 6,462,048.

Examples of SSRI's useful in the present combinations and methods may comprise, for example, fluoxetine (U.S. Pat. No. 4,314,081), paroxetine (U.S. Pat. No. 4,007,196), sertraline (U.S. Pat. No. 4,536,518), fluvoxamine (U.S. Pat. No. 4,085,225), venlafaxine hydrochloride (EFFEXOR®, U.S. Pat. No. 4,535,186), nefazodone hydrochloride (SERZONE®, U.S. Pat. No. 4,338,317), and bupropion hydrochloride (WELLBUTRIN®, U.S. Pat. Nos. 3,819,706 and 3,885,046).

Generally preferred anti-psychotic agents useful in the present combinations and methods may comprise, for example, ziprasidone (GEODON®, U.S. Pat. No. 5,312,925), olanzapine (U.S. Pat. No. 5,229,382), risperidone (U.S. Pat. No. 4,804,663), L-745,870, sonepiprazole, RP-62203 (fananserin), NGD-941, balaperidone, flesinoxan (U.S. Pat. No. 4,833,142), and gepirone (U.S. Pat. No. 4,423,049).

Generally preferred acetylcholinesterase inhibitors useful in the present combinations and methods may comprise, for example, donepezil (ARICEPT®, U.S. Pat. No. 4,895,841), rivastigmine (EXELON®, U.S. Pat. No. 4,948,807), metrifonate (U.S. Pat. No. 2,701,225), galanthamine, physostigmine, tacrine, huperzine, and icopezil (U.S. Pat. No. 5,538,984).

Generally preferred neuroprotectants useful in the instant combinations and methods may comprise, for example, NMDA receptor antagonists. Specific NMDA receptor antagonists comprise, for example, (1S,2S)-1-(4-hydroxyphenyl)-2-(4-hydroxy-4-phenylpiperidin-1-yl)-1-propanol (U.S. Pat. No. 5,272,160); eliprodil (U.S. Pat. No. 4,690,931); and gavestenel (U.S. Pat. No. 5,373,018). Examples of additional NMDA antagonists are disclosed in, for example, U.S. Pat. Nos. 4,690,931; 5,185,343; 5,272,160; 5,356,905; 5,373,018; 5,744,483; 5,962,472; 6,046,213; 6,124,317; 6,124,323; 6,130,234; 6,218,404; 6,333,036; and 6,448,270; and in PCT International Application Publication Nos. WO 97/23202 and WO 98/18793.

A generally preferred potassium channel modulator comprises, for example, BMS-204352 (flindokaliner, U.S. Pat. No. 5,602,169).

The disclosures of all of the above U.S. patents are incorporated herein by reference in their entirety.

In another aspect, the invention provides methods for inhibiting glycogen synthase kinase-3 activity in a mammal in need of such inhibition which methods comprise administering a glycogen synthase kinase-3 inhibiting amount of a compound of formula (I), a prodrug thereof, or a pharmaceutically acceptable salt of the compound or prodrug; or a pharmaceutical composition comprising a compound of formula (I), a prodrug thereof, or a pharmaceutically acceptable salt of the compound or prodrug, and a pharmaceutically acceptable carrier, vehicle, or diluent.

The compounds of formula (I), the prodrugs thereof, and the pharmaceutically acceptable salts of the compounds and prodrugs, may be administered to a mammal at dosage levels in the range of from about 0.0001 mg to about 1,000 mg per day. For a normal adult human having a body mass of about 70 kg, a dosage in the range of from about 0.01 mg to about 500 mg per kg body mass is typically sufficient. However, some variability in the general dosage range may be required depending upon the age and mass of the subject being treated, the intended route of administration, the particular compound being administered, and the like. The determination of dosage ranges and optimal dosages for a particular mammalian subject is within the ability of one of ordinary skill in the art having benefit of the instant disclosure.

According to the methods of the present invention, the compounds of formula (I), the prodrugs thereof, and the pharmaceutically acceptable salts of the compounds and prodrugs, or the aforementioned combinations thereof with the amounts of one or more of: (i) an anti-angiogenesis agent, (ii) a signal transduction inhibitor, (iii) an anti-proliferative agent, (iv) an NK-1 receptor antagonist, (v) a 5HT1$_D$ receptor antagonist, (vi) a selective serotonin reuptake inhibitor (SSRI), (vii) an anti-psychotic agent, (viii) an acetylcholinesterase inhibitor, (ix) a neuroprotectant, (x) tissue plasminogen activator (TPA), (xi) neutrophil inhibitory factor (NIF), and (xii) a potassium channel modulator, are preferably administered in the form of a pharmaceutical composition comprising a pharmaceutically acceptable carrier, vehicle, or diluent. Accordingly, a compound of formula (I), a prodrug thereof, or a pharmaceutically acceptable salt of the compound or prodrug, or the aforementioned combinations, may be administered to a subject separately, or together, in any conventional oral, rectal, transdermal, parenteral (e.g., intravenous, intramuscular, or subcutaneous), intracisternal, intravaginal, intraperitoneal, intravesical, local (e.g., powder, ointment, or drop), or buccal, or nasal dosage form.

Pharmaceutical compositions suitable for parenteral injection may comprise pharmaceutically acceptable sterile aqueous or nonaqueous solutions, dispersions, suspensions or emulsions, and sterile powders for extemporaneous reconstitution into sterile injectable solutions or dispersions. Examples of suitable aqueous and nonaqueous carriers, vehicles, and diluents include water, ethanol, polyols (such as propylene glycol, polyethylene glycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions, and by the use of surfactants.

The pharmaceutical compositions of the invention may further comprise adjuvants, such as preserving, wetting, emulsifying, and dispersing agents. Prevention of microorganism contamination of the instant compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of of injectable pharmaceutical compositions may be effected by the use of agents capable of delaying absorption, for example, aluminum monostearate and gelatin.

Solid dosage forms for oral administration include capsules, tablets, powders, and granules. In such solid dosage forms, the active compound is admixed with at least one inert conventional pharmaceutical excipient (or carrier) such as sodium citrate or dicalcium phosphate, or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid certain complex silicates, and sodium carbonate; (e) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and/or (i) lubricants, as for example, talc, calcium stearate, magnesium stearate, solid polyethylene glycols, sodium lauryl sulfate, or mixtures thereof. In the case of capsules and tablets, the dosage forms may further comprise buffering agents.

Solid compositions of a similar type may also be employed as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings and shells, such as enteric coatings and others well-known to one of ordinary skill in the art. They may also comprise opacifying agents, and can also be of such composition that they release the active compound(s) in a delayed, sustained, or controlled manner. Examples of embedding compositions that can be employed are polymeric substances and waxes. The active compound(s) can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the pharmaceutical composition can also include adjuvants, such as wetting agents, emulsifying and suspending agents, sweetening, flavoring, and perfuming agents.

Suspensions, in addition to the active compound(s), may further comprise suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or vaginal administration preferably comprise suppositories, which can be prepared by mixing an active compound(s) with suitable non-irritating excipients or carriers such as cocoa butter, polyethylene glycol or a suppository wax, which are solid at ordinary room temperature, but liquid at body temperature, and therefore, melt in the rectum or vaginal cavity thereby releasing the active component.

Dosage forms for topical administration may comprise ointments, powders, sprays and inhalants. The active agent(s) are admixed under sterile condition with a pharmaceutically acceptable carrier, vehicle, or diluent, and any preservatives, buffers, or propellants that may be required.

The compounds of formula (I) may be prepared according to the exemplary synthetic routes disclosed in Schemes 1 through 6 hereinbelow, as well as by other conventional organic preparative methods known to one of ordinary skill in the relevant art. It is to be understood that the methods disclosed in the instant Schemes are intended for purposes of exemplifying the instant invention, and are not to be construed in any manner as limitations thereon.

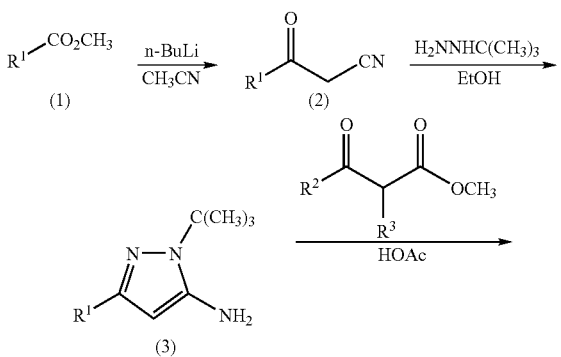

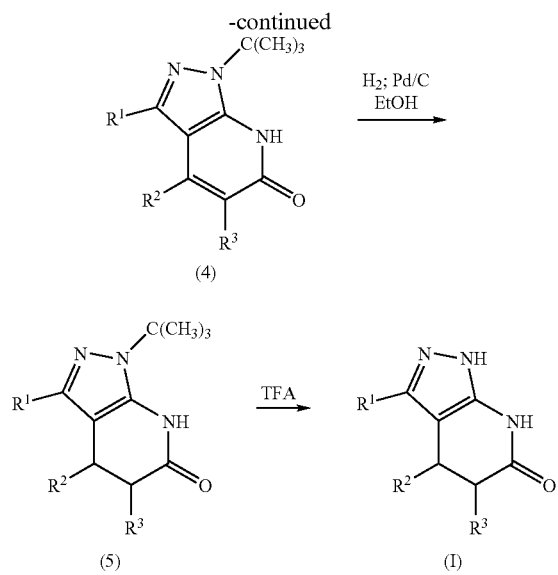

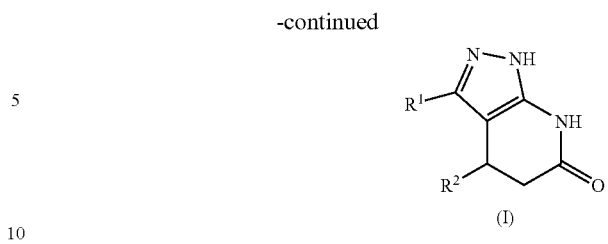

In Scheme 1, an appropriately-substituted methyl ester (1) is reacted with acetonitrile in the presence of a strong base, such as n-butyllithium, to afford α-cyanoketone (2). The reaction is normally effected in an aprotic solvent, such as tetrahydrofuran, at below ambient temperature, preferably at about −78° C. The resulting α-cyanoketone (2) is cyclocondensed with tert-butylhydrazine to afford protected aminopyrazole (3). The cyclocondensation is usually performed in a polar, protic solvent, such as ethanol at elevated temperature, preferably the reflux temperature of the solvent employed. The aminopyrazole (3) is then condensed with an appropriately-substituted di-ketoester to provide the dihydropyrazolo[3,4-b]pyridin-6-one derivative (4). The condensation is typically effected in a polar, protic solvent, such as glacial acetic acid, at elevated temperature, preferably between about 70-100° C. The hydrogenation of (4) is preferably effected a polar, protic solvent, such as ethanol, in the presence of a catalytic amount of palladium on carbon. Removal of the tert-butyl protecting group, preferably with trifluoroacetic acid (TFA) in a non-polar solvent, such as dichloroethane, affords (I).

Alternatively, the compounds of formula (I), wherein $R^3$ is hydrogen, may be prepared according to the exemplary synthetic route disclosed in Scheme 2 hereinbelow. Related synthetic routes for the preparation of compounds of formula (I) wherein $R^1$ comprises specifically enumerated groups, and $R^3$ is hydrogen, are disclosed hereinbelow in Schemes 3 through 6.

Scheme 2

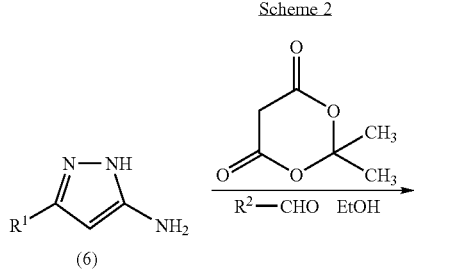

In Scheme 2, an appropriately-substituted aminopyrazole derivative (6), is cyclocondensed with 2,2-dimethyl-1,3-dioxane-4,6-dione (Meldrum's Acid) and an appropriately-substituted aldehyde $R^2$—CHO to afford (I). The cyclocondensation is preferably effected in a polar, protic solvent, such as ethanol, at elevated temperature, preferably at, or about, the reflux temperature of the particular solvent employed. See, for example, J. Quiroga, et al., Heterocyclic Comm., 5 (2), 115-122 (1999), and the references cited therein. The aminopyrazole starting materials (6) may be prepared according to known methods or, alternatively, according to the method in Scheme 1, wherein hydrazine is substituted for tert-butyl hydrazine in the second step of the preparative sequence.

The compounds of formula (I) wherein $R^1$ comprises a substituted cycloalkyl group, preferably a substituted cyclobutyl group, may be conveniently prepared as disclosed in Schemes 3 through 6 hereinbelow.

The compounds of formula (I), wherein $R^1$ comprises a cycloalkyl group, preferably a cyclobutyl group substituted with —$NR^4C(=O)R^5$, wherein $R^4$ is hydrogen, may be prepared as outlined hereinbelow in exemplary Scheme 3.

Scheme 3

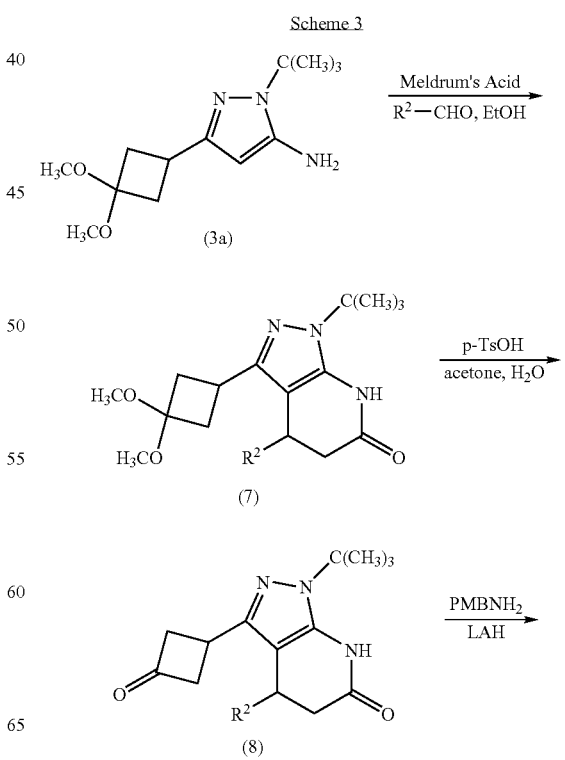

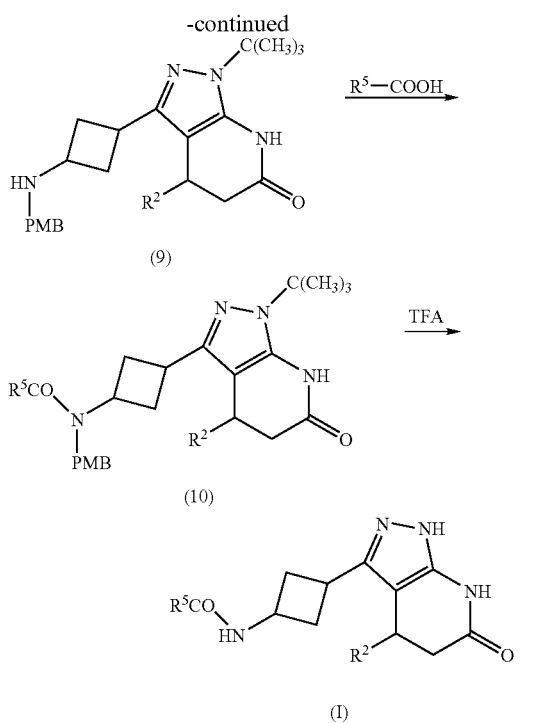

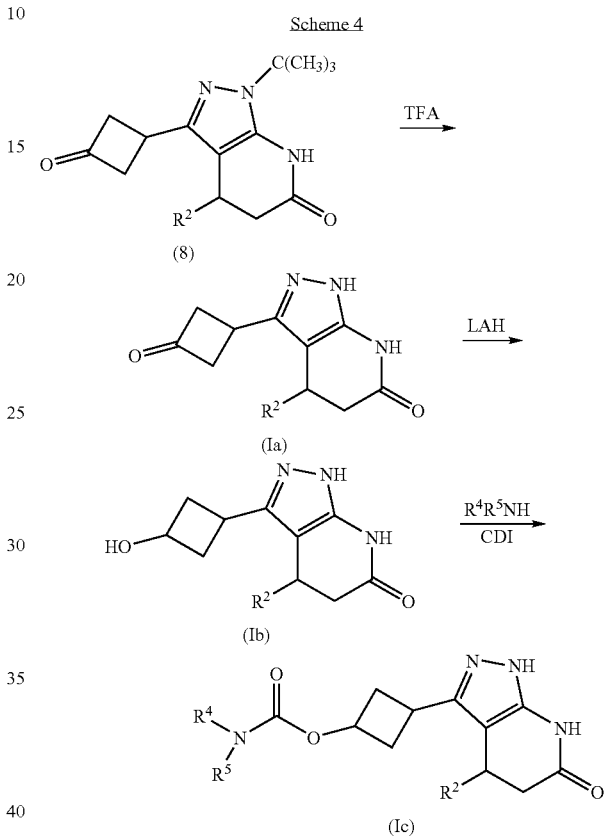

In Scheme 3, protected pyrazole (3a) is cyclocondensed with Meldrum's Acid and an aldehyde of the formula R²—CHO as described hereinabove in Scheme 2. The resulting dimethoxy compound (7) is then deprotected under standard conditions to afford ketone (8). For example, by treating a solution of (7) in a reaction-inert solvent, such as acetone, with an acid, such as hydrogen chloride, p-toluenesulfonic acid monohydrate, or pyridinium p-toluenesulfonate, at a temperature between about room temperature and about 80° C. Preferably, the deprotection is effected at about 65° C. Reductive amination of (8) with a protected amine, preferably 4-methoxy-benzylamine (PMB—NH$_2$), in a reaction of inert solvent, preferably toluene or tetrahydrofuran, at a reaction temperature of between about room temperature and about 150° C. preferably at the reflux temperature of the solvent employed, affords amine (9). The reduction is typically effected in a reaction-inert solvent at a temperature of between about room temperature and about 50° C. with a reducing reagent, preferably sodium triacetoxyborohydride, sodium cyanoborohydride, or lithium aluminum hydride. Amine (9) is then coupled, in the presence of a trialkylamine base, such as triethylamine or diisopropylethylamine, with a carbonyl donor, such as an alkyl chloroformate, an acid chloride, an acid anhydride, or an activated carboxylic acid derivative prepared from a carboxylic acid and an activating reagent, such as a polymer-supported coupling agent, or, alternatively, dicyclohexylcarbodiimide, 1,1-carbonyldiimidazole, tripropylphosphonic anhydride, an alkyl chloroformate, bis-(2-oxo-3-oxazolidinyl)phosphinic chloride, or benzotriazol-1-yloxy-tris(dimethylamino)phosphonium hexafluorophosphate, in a reaction-inert solvent, such as methylene chloride, pyridine, tetrahydrofuran, or diethyl ether. Preferably, the activating agent tripropylphosphonic anhydride and triethylamine are employed at a temperature of between about −78° C. and about 40° C. Compound (10) is then deprotected to afford (I) with trifluoroacetic acid either neat, or in a reaction-inert solvent, such as 1,2-dichloroethane, at a reaction temperature of between about 20° C. and about 100° C., preferably between about 65° C. to 75° C.

The compounds of formula (I), wherein R¹ comprises a cycloalkyl group, preferably a cyclobutyl group, substituted with —OH or —OC(=O)NR⁴R⁵, may be prepared as outlined hereinbelow in exemplary Scheme 4.

In Scheme 4, ketone (8) from Scheme 3 is deprotected, as disclosed in Scheme 1, to afford ketone (Ia). The reduction of ketone (Ia) to afford alcohol (Ib) may be effected according to known methods. The reduction is typically performed with a hydride reducing agent, for example, sodium triacetoxyborohydride, sodium cyanoborohydride, or lithium aluminum hydride in a reaction-inert solvent at a temperature of between about −78° C. to the reflux temperature of the solvent employed. The reduction is preferably performed using lithium aluminum hydride in tetrahydrofuran, at between about −78° C. and about room temperature. The functionalization of alcohol (I) with a carbonyl donor to form carbamate (Ic) is conveniently performed in the presence of a reaction of inert solvent, such as ethyl acetate, tetrahydrofuran, dimethylformamide, or diethyl ether. Preferred carbonyl donors comprise isocyanates, carbamoyl chlorides, or activated carbamoyl derivatives, including those disclosed hereinabove in Scheme 3, at a temperature of between about room temperature and the reflux temperature of the solvent employed.

The compounds of formula (I), wherein R¹ comprises a cycloalkyl group, preferably a cyclobutyl group, substituted with various aryl or heteroaryl groups, maybe prepared as outlined herein below in exemplary Scheme 5.

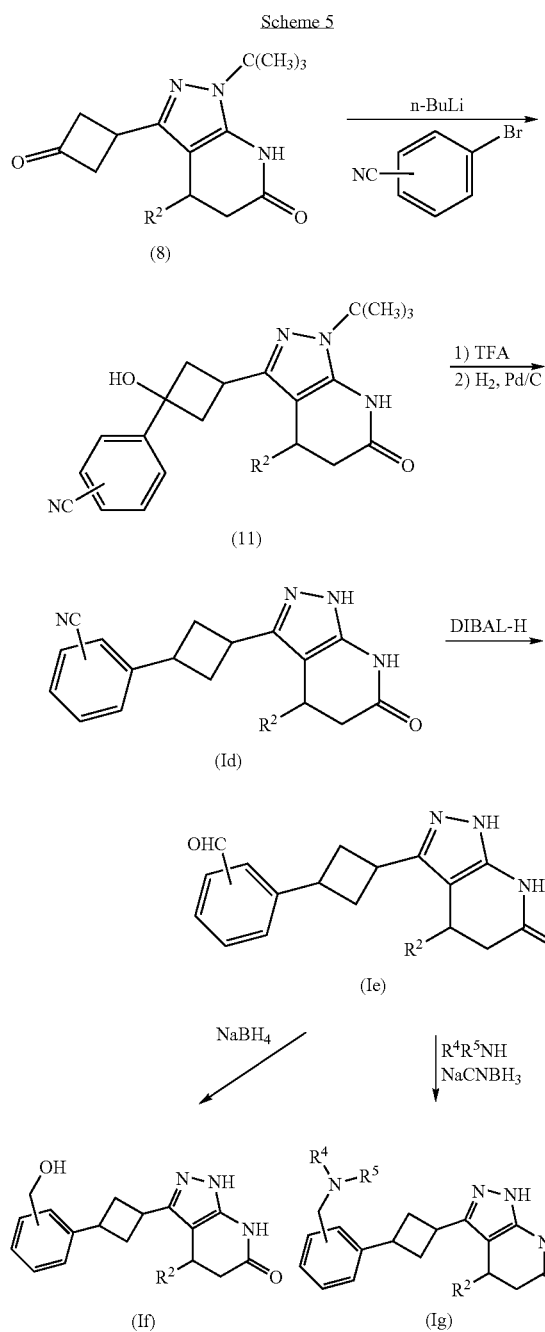

such as methylene chloride, chloroform, or 1,2-dichloroethane, in the presence of a silane, preferably triethylsilane or triphenylsilane, at a temperature from about −10° C. to about 50° C., where about room temperature to about 40° C. is preferred. Alternatively, and preferably, the alcohol moiety of (11) can be removed using a two-step procedure. Alcohol (11) is first treated with an acid, preferably methanesulfonic acid, in an inert solvent, such a 1,2-dichlorethane, at between about room temperature and about the reflux temperature of the solvent employed. Reduction of the resulting intermediate olefin to give nitrile (Id) is accomplished under standard hydrogenation conditions, preferably using palladium on carbon in the presence of hydrogen, at a pressure of 45 psi. Reduction of (Id) to form aldehyde (Ie) can be accomplished using a reducing reagent, preferably diisobutylaluminum hydride, in a reaction-inert solvent, preferably methylene chloride, at a temperature of between about −78° C. and about room temperature, preferably at about −78° C. The reduction of (Ie) to form alcohol (If) may be accomplished according to known methods. Preferably, aldehyde (Ie) is reacted with sodium borohydride, in a lower alcohol solvent, such as methanol, at room temperature. Alternatively, (Ie) may be reductively aminated with a primary or secondary amine to afford amine (Ig) as disclosed hereinabove in Scheme 3. Preferably, the reductive amination is effected with sodium cyanoborohydride in tetrahydrofuran.

Alternatively, the compounds of formula (I), wherein $R^1$ comprises a cycloalkyl group, preferably a cyclobutyl group, substituted with various aryl or heteroaryl groups, maybe prepared as outlined herein below in exemplary Scheme 6.

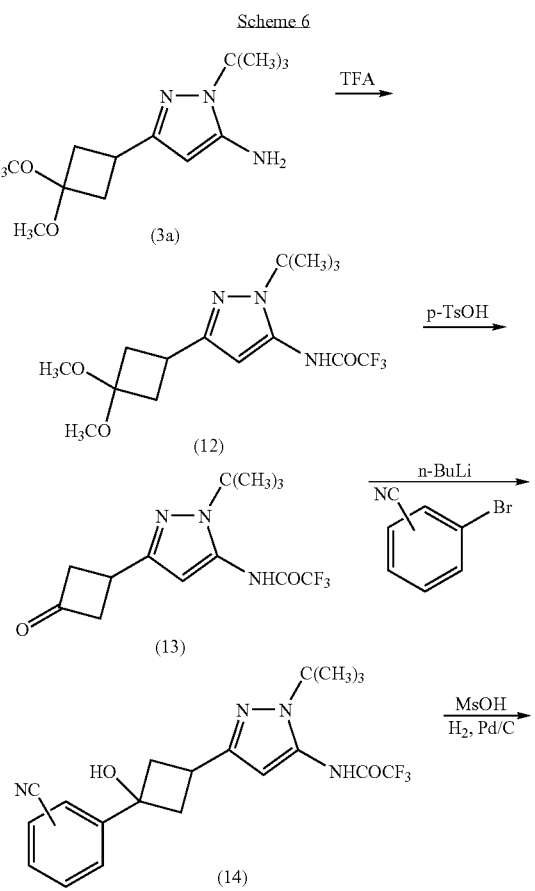

In Scheme 5, ketone (8) from Scheme 3 is reacted with a bromocyanobenzene derivative in the presence of an organometallic reagent, such as an organolithium, organomagnesium halide, organocerium, organotitanium, organozinc, organocopper, or organoaluminum reagent, to form alcohol (11). An organomagnesium halide (Grignard reagent) or organolithium reagent is preferred. The reaction is typically effected in a reaction-inert solvent, such as tetrahydrofuran, at a temperature of between about −78° C. and about 40° C., where between about −78° C. and about 0° C. is preferred. Removal of the alcohol moiety of (11) to give nitrile (Id) may be accomplished by reacting (11) with an acid, preferably trifluoroacetic acid, either neat, or in an inert solvent,

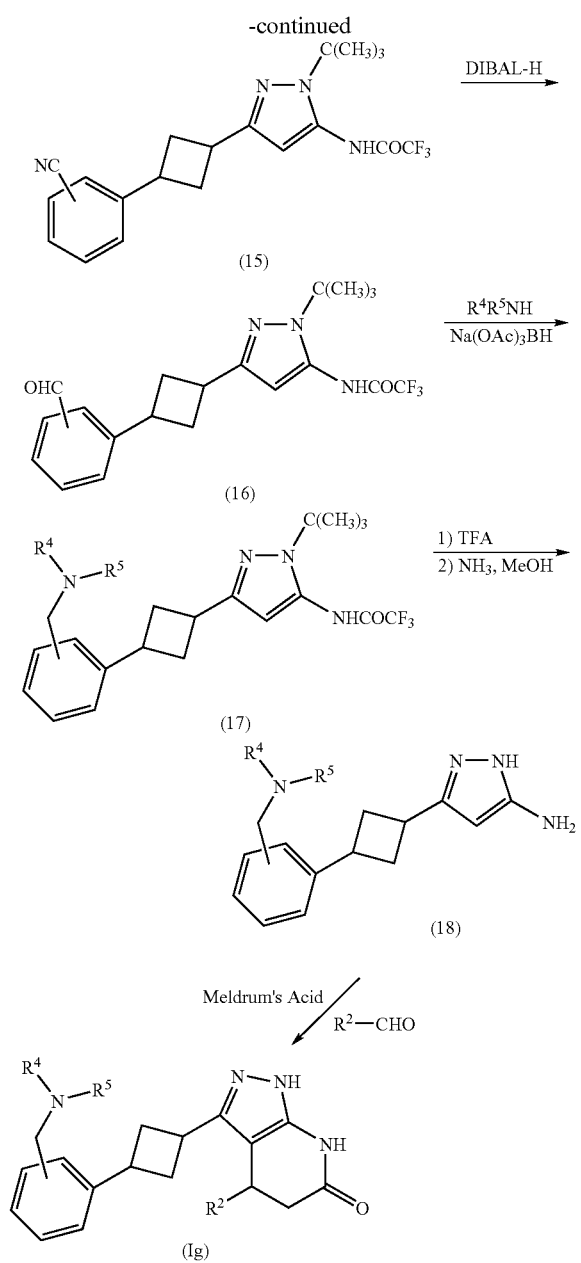

(17) to afford aminopyrazole (18) can be accomplished using conventional methods. For example, removal of the tert-butyl protecting group may be removed by reacting (17) with an acid, preferably trifluoroacetic acid, either neat, or in a reaction-inert solvent, such as methylene chloride, at between about room temperature and about 100° C., preferably from about 65° C. to 75° C. Similarly, removal of the trifluoroacetate protecting group may be accomplished by reacting (17) with a methanolic solution of ammonia at about room temperature. Aminopyrazole (18) is then cyclocondensed with Meldrum's Acid and an appropriately-substituted aldehyde $R^2$—CHO to afford (Ig).

Preparative Experimental

Unless otherwise noted, the following experimental abbreviations have the meanings indicated:
APCI—atmospheric pressure chemical ionization
n-BuLi—n-butyllithium
CDI—1,1'-carbonyldiimidazole
DCE—dichloroethane
DIBAL-H—diisobutylaluminum hydride
DMAP—4-dimethylaminopyridine
DMF—N,N-dimethylformamide
DMSO—dimethylsulfoxide
EtOAc—ethyl acetate
EtOH—ethanol
HPLC—high-performance liquid chromatography
hr—hour(s)
LAH—lithium aluminum hydride
LRMS—low resolution mass spectrometry
MeOH—methanol
min—minute(s)
mL—milliliter(s)
mmol—millimole(s)
MPLC—medium-pressure liquid chromatography
MS—mass spectrometry
NMR—nuclear magnetic resonance
THF—tetrahydrofuran
TLC—thin layer chromatography
TFA—trifluoroacetic acid Preparation 1

5-Cyclobutyl-1H-pyrazol-3-ylamine

In Scheme 6, aminopyrazole (3a) is first protected by the reaction thereof with trifluoroacetic acid in the presence of a coupling agent to give ketal (12). Preferably, the reaction is performed at room temperature in ethyl acetate using the coupling agent 1-propanephosphonic acid cyclic anhydride. Removal of the ketal protecting group of (12) to afford ketone (13) may be accomplished by known methods. Preferably, (12) is treated with p-toluenenesulfonic acid monohydrate in acetone, at a temperature of about 65° C. Ketone (13), is then reacted with a bromocyanobenzene derivative and an organometallic reagent as disclosed hereinabove in Scheme 5, to afford alcohol (14), which is subsequently dehydroxylated to provide nitrile (15), and reduced to aldehyde (16), also as described hereinabove in Scheme 5. Reductive amination of (16) with an amine, and sodium triacetoxyborohydride, gives amine (17). Removal of the tert-butyl and trifluoroacetate protecting groups of Step A To 800 mL of THF at −78° C. was added n-BuLi (312.0 mL, 780.0 mmol, 2.5 M in hexanes). After the reaction temperature equilibrated (~15 min), a solution of acetonitrile (40.7 mL, 780.0 mmol in 100 mL of THF) was added dropwise via an addition funnel over a 20 min period. The resulting milky white slurry was allowed to stir for 1 hr before a solution of ethyl cyclobutanecarboxylate (53.9 mL, 390.1 mmol in 150 mL of THF) was added down the side of the flask over a 20 min period. After one hr, the reaction was warmed to −45° C. (acetonitrile/$CO_2$) and allowed to stir for two hr. The reaction was quenched cold by the dropwise addition of 2 N HCl (~390 mL), pH=7 and then diluted with EtOAc (1 L). The layers were separated and the aqueous layer was extracted with $CH_2Cl_2$ (2×600 mL). The combined organic layers were dried over $MgSO_4$, filtered, and concentrated under reduced pressure to yield 3-cyclobutyl-3-oxo-propionitrile (quantitative yield) as a yellow oil that was used without further purification. $R_f$ 0.32 (40% EtOAc/hexanes). m/z (APCI$^+$) 138 (M−1).

Step B

To an aliquot of the crude 3-cyclobutyl-3-oxo-propionitrile (10.0 g, 81.3 mmol) prepared above in EtOH (300 mL) was added hydrazine. The resulting mixture was heated to 75° C. (oil bath). After 14 hr, the reaction was cooled to room temperature and concentrated under reduced pressure. The resulting oil was taken up in EtOAc and washed with saturated aqueous NaHCO$_3$ solution. The layers were separated and the aqueous layer was extracted with EtOAc. The combined organic layers were dried over MgSO$_4$, filtered through a pad of diatomaceous earth, and concentrated under reduced pressure. Purification of this material was accomplished by flash column chromatography on a Biotage® 75S MPLC system (A Dynax Corp., Charlottesville, Va.), eluting with 100 EtOAc (2 L) and 10% MeOH/CH$_2$Cl$_2$ (2 L). The product-containing fractions were collected and concentrated to give the title compound (10.0 g, 91% yield) as a brown oil. 400 MHz $^1$H NMR (CDCl$_3$) d 5.47 (s, 1H), 5.25 (bs, 3H), 3.40 (dddd, J=8.3, 8.3, 8.3, 8.3 Hz, 1H), 2.34-2.27 (m, 2H), 2.16-1.88 (m, 4H). LRMS m/z (APCI$^+$) 138 (M+1).

EXAMPLE 1

4-(4-Chloro-phenyl)-3-cyclobutyl-2,4,5,7-tetrahydro-pyrazolo[3,4-b]pyridin-6-one To 5-cyclobutyl-1H-pyrazol-3-ylamine (1.0 g, 7.3 mmol) in EtOH (20 mL) was added 4-chlorobenzaldehyde (1.1 g, 8.0 mmol) followed by Meldrum's Acid (1.1 g, 8.0 mmol). The reaction mixture was then heated to 75° C. (oil bath). After 30 min, the reaction was cooled to room temperature, the solid was filtered off, and then washed with MeOH (5 mL) and hexanes (10 mL). The solid was collected and dried under reduced pressure to give the title compound (1.3 g, 59% yield) as a colorless solid. 500 MHz $^1$H NMR (DMSO-d$_6$) d 12.0 (s, 1H), 10.3 (s, 1H), 7.34 (d, J=8.7 Hz, 2H), 7.11 (d, J=8.3 Hz, 2H), 4.20 (dd, J=7.1, 4.2 Hz, 1H), 3.17 (dddd, J=8.7, 8.7, 8.7, 8.7 Hz, 1H), 2.84 (dd, 15.8, 7.1 Hz, 1H), 2.44 (dd, J=16.2, 4.6 Hz, 1H), 2.09-1.87 (m, 4H), 1.83-1.69 (m, 1H), 1.68-1.61 (m, 1H). $^{13}$C NMR (125 Mz, DMSO-d$_6$) d 169.8, 149.5, 144.1, 142.8, 131.7, 129.4, 129.2, 101.1, 41.3, 33.9, 31.0, 28.8, 28.4, 18.7. LRMS m/z (APCI$^+$) 303 (M+1).

The following compounds were prepared in a manner analogous to that described in Example 1 using appropriate starting materials.

EXAMPLE 2

3-Cyclobutyl-4-phenyl-2,4,5,7-tetrahydro-pyrazolo[3,4-b]pyridin-6-one

500 MHz $^1$H NMR (DMSO-d$_6$) d 12.0 (s, 1H), 10.3 (s, 1H), 7.25 (dd, J=7.5, 1.2 Hz, 2H), 7.18 (dddd, J=6.6, 6.6, 1.2, 1.2 Hz, 1H), 7.10 (dd, J=8.3, 1.2 Hz, 2H), 4.17 (dd, J=7.1,4.6 Hz, 1H), 3.15 (dddd, J=8.7, 8.7, 8.7, 8.7 Hz, 1H), 2.81 (dd, J=15.8, 7.5 Hz, 1H), 2.47 (dd, J=15.7, 5.0 Hz, 1H), 2.50-2.45 (m, 1H), 2.09-1.84 (m, 4H), 1.80-1.71 (m, 1H), 1.68-1.60 (m, 1H). $^{13}$C NMR (125 Mz, DMSO-d$_6$) d 170.1, 149.5, 145.0, 142.7, 129.2, 127.5, 127.2, 101.5, 41.4, 34.6, 34.5, 31.0 28.5, 18.7. LRMS m/z (APCI$^+$) 268.3 (M+1).

EXAMPLE 3

3-Cyclobutyl-4-(4-methoxy-phenyl)-2,4,5,7-tetrahydro-pyrazolo[3,4-b]pyridin-6-one 300 MHz $^1$H NMR (DMSO-d$_6$) d 12.0 (s, 1H), 10.3 (s, 1H), 7.00 (d, J=8.7 Hz, 2H), 6.82 (d, J=8.7 Hz, 2H), 4.11 (dd, J=6.6, 4.6 Hz, 1H), 3.69 (s, 3H), 3.15 (dddd, 8.7, 8.7, 8.7, 8.7 Hz, 1H), 2.79 (dd, J=15.8, 7.1 Hz, 1H), 2.43 (dd, J=15.8, 4.6 Hz, 1H), 2.09-1.87 (m, 4H), 1.82-1.72 (m, 1H), 1.70-1.60 (m, 1H). 125 MHz $^{13}$C NMH (DMSO-d$_6$) d 170.1, 158.5, 149.5,142.6, 136.9, 128.5, 114.5, 101.8, 55.7, 41.7, 33.7, 28.8, 28.5, 18.7. LRMS m/z (APCI$^+$) 298.2 (M+1).

EXAMPLE 4

3-Cyclobutyl-4-(2,4,5-trifluoro-phenyl)-2,4,5,7-tetrahydro-pyrazolo[3,4-b]pyridin-6-one 500 MHz $^1$H NMR (DMSO-d$_6$) d 12.1 (s, 1H), 10.4 (s, 1H), 7.55 (ddd, J$_{H-F}$=10.4, 10.4, 6.6 Hz, 1H), 6.90 (ddd, J$_{H-F}$ 11.2, 9.1, 7.1 Hz, 1H), 4.41 (dd, J=7.5, 5.0 Hz, 1H), 3.15 (dddd, J=8.3, 8.3, 8.3, 8.3 Hz, 1H), 2.87 (dd, J=16.2, 7.5 Hz, 1H), 2.43 center outer d (dd, J=DMSO masked, 4.6 Hz, 1H), 2.11-1.73 (m, 5H), 1.70-1.62 (m, 1H). LRMS m/z (APCI$^+$) 322 (M+1).

EXAMPLE 5

3-Cyclobutyl-4-ethyl-2,4,5,7-tetrahydro-pyrazolo[3,4-b]pyridin-6-one

500 MHz $^1$H NMR (CDCl$_3$) d 10.44 (bs, 1H), 3.56 (dddd, J=8.3, 8.3, 8.3, 8.3 Hz, 1H), 2.85-2.72 (m, 2H), 2.61 (dd, J=15.8, 2.1 Hz, 1H), 2.40-2.34 (m, 4), 1.52 (dddd, J=7.1, 7.1, 7.1, 7.1 Hz, 2H), 0.90 (t, J=7.5 Hz, 3H).

EXAMPLE 6

3-Cyclobutyl-4-isopropyl-2,4,5,7-tetrahydro-pyrazolo[3,4-b]pyridin-6-one

500 MHz $^1$H NMR (CDCl$_3$) d 10.58 (bs, 1H), 3.54 (dddd, 8.7, 8.7, 8.7, 8.7 Hz, 1H), 2.71 (m, 3H), 2.38-2.29 (m, 4H), 2.09-1.95 (m, 2H), 1.95-1.75 (m, 1H); 0.90-0.87 (m, 6H).

EXAMPLE 7

3-Cyclobutyl-4-propyl-2,4,5,7-tetrahydro-pyrazolo[3,4-b]pyridin-6-one

500 MHz $^1$H NMR (CDCl$_3$) d 10.55 (bsm 1H), 3,54 (dddd, 9.1, 9.1, 9.1, 9.1 Hz, 1H), 2.92-2.86 (m, 1H), 2.78 (dd, J=16.2, 7.1 Hz, 1H), 2.59 (dd, J=16.2, 2.5 Hz, 1H), 2.38-2.29 (m, 4H), 2.12-2.05 (m, 2H), 2.01-1.95 (m, 2H), 1.37-121 (m, 2H), 0.89 (t, 7.1 Hz, 3H); 0.89 (t, J=7.1 Hz, 3H).

EXAMPLE 8

Cyclobutyl-4-(1H-imidazol-4-yl)-2,4,5,7-tetrahydro-pyrazolo[3,4-b]pyridin-6-one

500 MHz $^1$H NMR (CDCl$_3$) d 11.86 (bs, 1H), 10.10 (s, 1H), 7.52 (s, 1H), 6.44 (s, 1H), 4.05 (dd, J=5.4, 5.4 Hz, 1H), 2.73-2.63 (m, 2H), 2.16-1.96 (m, 4H), 1.95-1.76 (m, 1H), 1,74-1.66 (m, 1H).

EXAMPLE 9

3-Cyclobutyl-4-isobutyl-2,4,5,7-tetrahydro-pyrazolo[3,4-b]pyridin-6-one

500 MHz $^1$H NMR (CDCl$_3$) d 10.50 (bs, 1H), 3.54 (dddd, J=8.7, 8.7, 8.7, 8.7 Hz, 1H), 2.97-2.90 (m, 1H), 2.76 (dd, J=15.8, 6.6 Hz, 1H), 2.59 (dd, J=15.8, 2.1 Hz, 1H), 2.36 (dddd, 15.3, 8.7, 8.7, 8.7 Hz, 4H), 2.08-1.95 (m, 2H), 1.56 (dddd, J=19.5, 8.7 8.7, 8.7, 8.7 Hz, 1H), 1.56 (dddd, 13.3, 13.3, 6.6, 6.6 Hz, 1H), 1.33 (ddd, J=13.3, 13.3, 5.4 Hz, 2H), 0.95 (d, J=6.2 Hz, 3H), 0.88 (d, J=6.2 Hz, 3H

EXAMPLE 10

3-Cyclobutyl-4-(4-trifluoromethyl-phenyl)-2,4,5,7-tetrahydro-pyrazolo[3,4-b]pyridin-6-one 500 MHz $^1$H NMR (CDCl$_3$) d 10.82 (bs, 1H), 7.59 (d, J=8.3 Hz, 2H), 7.30 (d, J=8.3 Hz, 2H), 4.30 (dd, J=5.2, 5.2 Hz, 1H), 3.22 (dddd, J=8.8, 8.8, 8.8, 8.8 Hz, 1H), 3.12 (dd, J=16.6, 7.8 Hz, 1H), 2.82 (dd, J=16.6, 5.2 Hz, 1H), 2.21-2.02 (m, 4H), 1.99-1.81 (m, 2H).

EXAMPLE 11

4-(3-Cyclobutyl-6-oxo-4,5,6,7-tetrahydro-2H-pyrazolo[3,4-b]pyridin-4-yl)-benzonitrile 500 MHz $^1$H NMR (CDCl$_3$) d 10.71(bs, 1H), 7.64 (d, J=8.3 Hz, 2H), 7.29 (d, J=8.8 Hz, 2H), 3.20 (dddd, J=8.8, 8.8, 8.8, 8.8 Hz, 1H), 3.11 (dd, J=16.1, 7.3 Hz, 1H), 2.8 (dd, 16.1, 5.2 Hz, 1H), 2.21-2.01 (m, 4H), 1.93 (dddd, J=19.2, 8.3, 8.3, 8.3 Hz, 1H), 1.89-1.81 (m, 1H);

EXAMPLE 12

3-Cyclobutyl-4-p-tolyl-2,4,5,7-tetrahydro-pyrazolo[3,4-b]pyridin-6-one

500 MHz $^1$H NMR (CDCl$_3$) d 10.65 (bs, 1H), 7.12 (d, J=8.3 Hz, 2H), 7.06 (d, J=7.9 Hz, 2H), 4.18 (dd, J=6.7, 6.7 Hz, 1H), 3.19 (dddd, J=8.8, 8.8, 8.8, 8.8 Hz, 1H), 3.04 (dd, J=16.6, 7.3 Hz, 1H), 2.82 (dd, 16.6, 6.2 Hz, 1H), 2.34 (s, 3H), 2.18-2.02 (m, 4H), 1.92-1.80 (m, 2H).

EXAMPLE 13

3-Cyclobutyl-4-(3-fluoro-phenyl)-2,4,5,7-tetrahydro-pyrazolo[3,4-b]pyridin-6-one 500 MHz $^1$H NMR (CDCl$_3$) d 10.60 (bs, 1H), 7.30 (ddd, J=7.4, 7.4, 6.2 Hz, 1H), 6.96 (dd, J=7.8, 1.6 Hz, 1H), 6.94 (d, J=2.6 Hz, 1H), 6.86 (d, J=9.3 Hz, 1H), 4.23 J=6.2 Hz, 1H), 3.23 (dddd, J=8.8, 8.8, 8.8, 8.8 Hz, 1H), 3.08 (dd, J=16.6, 7.8 Hz, 1H), 2.82 (dd, J=16.6, 5.7 Hz, 1H), 2.21-2.04 (m, 4H), 1.96-1.81 (m, 2H).

EXAMPLE 14

4-(2-Chloro-4-fluoro-phenyl)-3-cyclobutyl-2,4,5,7-tetrahydro-pyrazolo[3,4-b]pyridin-6-one 500 MHz $^1$H NMR (CDCl$_3$) d 10.97 (bs, 1H), 7.18 (dd, J=8.5, 2.6 Hz, 1H), 6.95 (dd, J=8.3, 5.7 Hz, 1H), 6.90 (ddd, J=7.8, 7.8, 2.6 Hz, 1H), 4.71 (dd, J=7.8, 4.2 Hz, 1H), 3.74 (dddd, J=8.8, 8.8, 8.8,8.8 Hz, 1H), 3.11 (dd, J=16.6, 7.8 Hz, 1H), 2.83 (dd, J=16.1, 4.2 Hz, 1H), 2.20-2.03 (m, 4H), 1.97-1.88 (m, 2H), 1.86-1.79 (m, 2H).

EXAMPLE 15

3-Cyclobutyl-4-(2-fluoro-phenyl)-2,4,5,7-tetrahydro-pyrazolo[3,4-b]pyridin-6-one 500 MHz $^1$H NMR (CDCl$_3$) d 10.67 (bs, 1H), 7.26-7.23 (m, 1H), 7.07 (dd, J=18.1, 10.9 Hz, 2H), 6.99 (ddd, J=7.8, 7.8, 1.6 Hz, 1H), 4.59 (dd, J=7.8, 4.7 Hz, 1H), 3.27 (dddd, J=8.8, 8.8, 8.8, 8.8 Hz, 1H), 3.10 (dd, J=16.6, 7.8 Hz, 2H), 2.19-2.10 (m, 4H), 1.95-1.79 (m, 2H).

EXAMPLE 16

3-Cyclobutyl-4-(4-methyl-naphthalen-1-yl)-2,4,5,7-tetrahydro-pyrazolo[3,4-b]pyridin-6-one 500 MHz $^1$H NMR (CDCl$_3$) d 10.69 (bs, 1H), 8.09 (dd, J=3.6, 3.6 Hz, 2H), 7.59 (dd, J=3.6, 3.6 Hz, 2H), 7.21 (d, 6.7 Hz, 1H), 7.04 (d, J=7.3 Hz, 1H), 5.04 (bs, 1H), 3.27-3.14 (m, 2H), 3.00 (dd, J=16.1, 0.0 Hz, 1H), 2.69 (s, 3H), 2.11 (dddd, 19.2, 9.6, 9.6, 9.6 Hz, 3H), 2.00 (m, 1H), 1.87 (m, 1H), 1.81-1.72 (m, 2H).

EXAMPLE 17

3-Cyclobutyl-4-(4-dimethylamino-2-fluoro-phenyl)-2,4,5,7-tetrahydro-pyrazolo[3,4-b]pyridin-6-one LRMS m/z (APCI$^+$) 229 (M+1).

EXAMPLE 18

3-Cyclobutyl-4-cyclohexyl-2,4,5,7-tetrahydro-pyrazolo[3,4-b]pyridin-6-one

500 MHz $^1$H NMR (CDCl$_3$) d L3.54 (dddd, J=8.8, 8.8, 8.8, 8.8 Hz, 1H), 2.76-2.69 (m, 3H), 2.40-2.56 (m, 4H), 2.12-1.96 (m, 2H), 1.77-1.59 (m, 5H), 1.39-0.92 (m, 6H); 125 MHz $^{13}$C NMR (CDCl$_3$) d 173.8, 148.2, 143.2, 101.5, 43.7, 35.8, 34.6, 41.4, 30.2, 29.9, 29.2, 28.9, 26.7, 26.6, 26.5,19.1. LRMS m/z (APCI$^+$) 274 (M+1).

EXAMPLE 19

3-Cyclobutyl-4-cyclohex-3-enyl-2,4,5,7-tetrahydro-pyrazolo[3,4-b]pyridin-6-one

500 MHz $^1$H NMR (CDCl$_3$) d 10.58 (bs, 1H), 5.64 (d, J=8.3 Hz, 2H), 3.60-3.50 (m, 1H), 2.88-1.20 (m, 16H). LRMS m/z (APCI$^+$) 272 (M+1).

EXAMPLE 20

4-sec-Butyl-3-cyclobutyl-2,4,5,7-tetrahydro-pyrazolo[3,4-b]pyridin-6-one

LRMS m/z (APCI$^+$) 247 (M+1).

EXAMPLE 21

4-Benzyloxymethyl-3-cyclobutyl-2,4,5,7-tetrahydro-pyrazolo[3,4-b]pyridin-6-one

500 MHz $^1$H NMR (CDCl$_3$) d 10.66 (s, 1H), 7.33-7.24 (m, 5H), 4.51 (s, 2H), 3.54 (dddd, J=8.8, 8.8, 8.8, 8.8 Hz, 1H), 3.47 (dd, J=16.1, 5.7 Hz, 1H), 3.44-3.38 (m, 1H), 3.25-32.8 (m, 1H), 2.92-2.78 (m, 2H), 2.38-2.20 (m, 4H), 2.08-1.90 (m, 2H). LRMS m/z (APCI$^+$) 312 (M+1).

EXAMPLE 22

4-Benzyl-3-cyclobutyl-2,4,5,7-tetrahydro-pyrazolo[3,4-b]pyridin-6-one

500 MHz $^1$H NMR (CDCl$_3$) d 10.74 (s, 1H), 7.31-7.20 (m, 3H), 7.09-7.06 (m, 2H), 3.14 (dddd, J=7.8, 7.8, 7.8, 2.1 Hz, 1H), 2.92-2.74 (m, 4H), 2.67 (dd, J=16.1, 2.6 Hz, 1H), 2.24-2.01 (m, 4H), 1.98-1.84 (m, 2H). LRMS m/z (APCI$^+$) 282 (M+1).

EXAMPLE 23

3-Cyclobutyl-4-(2-methylsulfanyl-ethyl)-2,4,5,7-tetrahydro-pyrazolo[3,4-b]pyridin-6-one 500 MHz $^1$H NMR (CDCl$_3$) d 12.09 (s, 1H), 10.66 (s, 1H), 3.64-3.54 (m, 1H), 3.14-3.06 (m, 1H), 2.89-2.82 (m, 1H), 2.60 (d, J=16.1 Hz, 1H), 2.48-2.26 (m, 6H), 2.10 (s, 3H), 2.04-1.96 (m, 1H), 1.84-1.62 (m, 3H). 125 MHz $^{13}$C NMR (CDCl$_3$) d 172.8, 147.6, 143.0, 102.1, 38.2, 35.0, 31.5, 31.2, 29.3, 28.8, 27.6, 19.1, 15.7. LRMS m/z (APCI$^+$) 266 (M+1).

EXAMPLE 24

2-(3-Cyclobutyl-6-oxo-4,5,6,7-tetrahydro-2H-pyrazolo[3,4-b]pyridin-4-yl)-cyclopropanecarboxylic acid ethyl ester LRMS m/z (APCI$^+$) 304 (M+1).

EXAMPLE 25

3-Cyclobutyl-4-cyclopropyl-2,4,5,7-tetrahydro-pyrazolo[3,4-b]pyridin-6-one

500 MHz $^1$H NMR (CDCl$_3$) d 12.03 (s, 1H), 10.52 (s, 1H), 3.64 (dddd, J=8.8, 8.8, 8.8, 8.8 Hz, 1H), 2.84 (dd, 15.6, 6.7 Hz, 1H), 2.72 (dd, J=16.1, 4.1 Hz, 1H), 2.47-2.27 (m, 5H), 2.12-1.96 (m, 2H), 0.93-0.86 (m, 1H), 0.53-0.47 (m, 2H), 0.24-0.10 (m, 2H). 125 MHz $^{13}$C NMR (CDCl$_3$) d 173.2, 148.2, 143.1, 101.4, 39.2, 33.2, 31.4, 29.6, 28.6, 19.0, 16.4, 4.0, 3.2. LRMS m/z(APCI$^+$) 332 (M+1).

EXAMPLE 26

3-Cyclobutyl-4-(4-ethyl-phenyl)-2,4,5,7-tetrahydro-pyrazolo[3,4-b]pyridin-6-one

500 MHz $^1$H NMR (CDCl$_3$) d 11.93 (s, 1H), 10.60 (s, 1H), 7.13 (d, J=7.8 Hz, 2H), 7.10 (d, J=7.8 Hz, 2H), 4.19 (dd, J=6.7, 6.7 Hz, 1H), 3.19 (dddd, J=8.8, 8.8, 8.8, 8.8 Hz, 1H), 3.05 (dd, J=16.1, 6.7 Hz, 1H), 2.84 (dd, J=16.1, 5.7 Hz, 1H), 2.63 (q, J=7.8 Hz, 2H), 2.18-2.00 (m, 4H), 1.92-1.78 (m, 2H), 1.23 (t, J=7.8 Hz, 3H). 125 MHz $^{13}$C NMR (CDCl$_3$) d 172.3, 148.2, 143.4, 143.1, 140.7, 128.4, 127.3, 101.7, 41.3, 34.8, 31.3, 28.6, 28.4, 28.2, 19.0, 15.8. LRMS m/z (APCI$^+$) 296 (M+1).

EXAMPLE 27

3-Cyclobutyl-4-o-tolyl-2,4,5,7-tetrahydro-pyrazolo[3,4-b]pyridin-6-one

500 MHz $^1$H NMR (CDCl$_3$) d 11.62 (s, 1H), 10.32 (s, 1H), 7.20-7.10 (m, 3H), 7.02-7.00 (m, 1H), 4.47 (dd, J=6.7, 6.7 Hz, 1H), 3.08 (dddd, J=8.8, 8.8, 8.8, 8.8 Hz, 1h), 3.01 (dd, J=16.1, 7.2 Hz, 1H), 2.73 (dd, J=16.6, 7.3 Hz, 1H), 2.42 (s, 3H), 2.08-1.94 (m, 4H), 1.88-1.72 (m, 2H). LRMS m/z (APCI$^+$) 282 (M+1).

EXAMPLE 28

4-(5-Chloro-2-methoxy-pyridin-3-yl)-3-cyclobutyl-2,4,5,7-tetrahydro-pyrazolo[3,4-b]pyridin-6-one 500 MHz $^1$H NMR (CDCl$_3$) d 10.81 (s, 1H), 7.99 (d, J=2.6 Hz, 1H), 7.05 (d, J=2.1 Hz, 1H), 4.44 (dd, J=7.8, 3.1 Hz, 1H), 4.00(s, 3H), 3.32 (dddd, J=8.8, 8.8, 8.8 8.8 Hz, 1H), 3.07 (dd, J=16.6, 7.8 Hz, 1H), 2.90 (dd, J=16.6, 3.1 Hz, 1H), 2.28-2.04 (m, 4H), 2.00-1.82 (m, 2H). 125 MHz $^{13}$C NMR (CDCl$_3$) d 172.0, 159.8, 148.9, 143.7, 136.3, 127.0, 124.5, 98.8, 54.1, 38.1, 31.1, 28.5, 28.0, 19.1. LRMS m/z (APCI$^+$) 333 (M+1).

EXAMPLE 29

4-(4-Chloro-5-methoxy-pyridin-2-yl)-3-cyclobutyl-2,4,5,7-tetrahydro-pyrazolo[3,4-b]pyridin-6-one LRMS m/z (APCI$^+$) 333 (M+1).

EXAMPLE 30

4-(2-Chloro-phenyl)-3-cyclobutyl-2,4,5,7-tetrahydro-pyrazolo[3,4-b]pyridin-6-one 500 MHz $^1$H NMR (CDCl$_3$) d 10.75 (s, 1H), 7.40 (dd, J=7.3, 1.6 Hz, 1H), 7.21-7.15 (m, 2H), 7.00 (dd, J=7.3, 2.1 Hz, 1H), 4.76 (dd, J=7.8, 4.1 Hz, 1H), 3.24 (dddd, J=8.8, 8.8, 8.8, 8.8 Hz, 1H), 3.11 (dd, J=16.6, 8.3 Hz, 1H), 2.85 (dd, J=16.6, 8.3 Hz, 1H), 2.14-2.01 (m, 4H), 1.94-1.76 (m, 2H). 125 MHz $^{13}$C NMR (CDCl$_3$) d 171.8, 149.0, 143.5, 140.6, 133.1, 130.0, 128.8, 128.6, 127.5, 101.3, 39.2, 31.3, 28.0, 19.0. LRMS m/z (APCI$^+$) 302 (M+1).

EXAMPLE 31

3-Cyclobutyl-4-(2,4-difluoro-phenyl)-2,4,5,7-tetrahydro-pyrazolo[3,4-b]pyridin-6-one 500 MHz $^1$H NMR (CDCl$_3$) d 10.98 (s, 1H), 6.97-9.92 (m, 1H), 6.87-6.75 (m, 2H), 4.54 (dd, J=7.3, 4.1 Hz, 1H), 3.28 (dddd, J=8.3, 8.3, 8.3, 8.3 Hz, 1H), 3.10 (dd, J=16.6, 7.8 Hz, 1H), 2.84 (dd, J=16.6, 4.1 Hz, 1H), 2.26-1.82 (m, 6H). LRMS m/z (APCI$^+$) 304 (M+1).

EXAMPLE 32

3-Cyclobutyl-4-naphthalen-2-yl-2,4,5,7-tetrahydro-pyrazolo[3,4-b]pyridin-6-one

500 MHz $^1$H NMR (CDCl$_3$) d 10.65 (s, 1H), 7.88-7.78 (m, 3H), 7.59 (s, 1H), 7.51-7.45 (m, 2H), 7.37 (dd, J=8.3, 1.6 Hz, 1H), 4.40 (dd, J=6.7, 6.7 Hz, 1H), 3.18 (dddd, J=8.8, 8.8, 8.8, 8.8 Hz, 1H), 3.15 (dd, J=16.6, 7.2 Hz, 1H), 2.95 (dd, J=16.6, 6.02 Hz, 1H), 2.19-1.97 (m, 4H), 1.85-1.75 (m, 2H). LRMS m/z (APCI$^+$) 318 (M+1).

EXAMPLE 33

3-Cyclobutyl-4-naphthalen-1-yl-2,4,5,7-tetrahydro-pyrazolo[3,4-b]pyridin-6-one

500 MHz $^1$H NMR (CDCl$_3$) d 12.2 (s, 1H), 10.9 (s, 1H), 8.12 (d, J=8.3 Hz, 1H), 7.92 (d, J=7.8 Hz, 1H), 7.77 (d, J=8.3 Hz, 1H), 7.58 (ddd, J=7.8, 7.8, 1.0 Hz, 1H), 7.54 (dd, J=8.3, 8.3 Hz, 1H), 7.38 (dd, J=7.3, 7.3 Hz, 1H), 7.13 (d, J=7.3 Hz, 1H), 5.06 (dd, J=7.3, 4.7 Hz, 1H), 3.26 (dd, J=16.6, 7.8 Hz, 1H), 3.11, (dddd, J=8.8, 8.8, 8.8, 8.8 Hz, 1H), 3.05 (dd, J=16.1, 4.7 Hz, 1H), 2.11-1.68 (m, 6H). LRMS m/z (APCI$^+$) 318 (M+1).

EXAMPLE 34

3-Cyclobutyl-4-(4-dimethylamino-2-methyl-phenyl)-2,4,5,7-tetrahydro-pyrazolo[3,4-b]pyridin-6-one 500 MHz $^1$H NMR (CDCl$_3$) d 10.0 (s, 1H), 6.87 (d, J=8.3 Hz, 1H), 6.57 (d, J=2.6 Hz, 1H), 6.52 (dd, J=8.3, 2.6 Hz, 1H), 4.37 (dd, J=7.3, 7.3 Hz, 1H), 3.10 (dddd, J=8.8, 8.8, 8.8, 8.8 Hz, 1H), 2.94 (dd, J=16.1, 7.3 Hz, 1H), 2.93 (s, 6H), 2.70 (dd, J=16.1, 7.3 Hz, 1H), 2.37 ((s, 3H), 2.09-1.98 (m, 4H), 1.87-1.75 (m, 2H). LRMS m/z (APCI$^+$) 325 (M+1).

EXAMPLE 35

4-(3-Cyclobutyl-6-oxo-4,5,6,7-tetrahydro-2H-pyrazolo[3,4-b]pyridin-4-yl)-benzoic acid methyl ester 500 MHz $^1$H NMR (CDCl$_3$) d 10.5 (s, 1H), 8.00 (d, J=8.3 Hz, 1H), 7.27 (d, J=8.8 Hz, 1H), 4.82 (dd, J=6.2, 6.2 Hz, 1H), 3.93 (s, 3H), 3.17 (dddd, J=8.8, 8.8, 8.8, 8.8 Hz, 1H), 3.09 (dd, J=16.6, 7.7 Hz, 1H), 2.82 (dd, J=16.5, 6.2 Hz, 1H), 2.12 (2.01 (m, 4H), 1.92-1.77 (m, 2H). LRMS m/z (APCI$^+$) 326 (M+1).

EXAMPLE 36

3-Cyclobutyl-4-(2,4-dimethyl-phenyl)-2,4,5,7-tetrahydro-pyrazolo[3,4-b]pyridin-6-one 500 MHz $^1$H NMR (CDCl$_3$) d 10.5 (s, 1H), 7.01 (s, 1H), 6.93 (d, J=8.3 Hz, 1H), 6.89 (d, J=7.7 Hz, 1H), 4.43 (dd, J=6.7, 6.7 Hz, 1H), 3.09 (dddd, J=8.3, 8.3, 8.3, 8.3 Hz, 1H), 2.99 (dd, J=16.1, 7.3 Hz, 1H), 2.71 (dd, J=16.1, 7.7 Hz, 1H), 2.38 (s, 3H), 2.30 (s, 3H), 2.08-1.97 (m, 4H), 1.87-1.79 (m, 2H). 125 MHz $^{13}$C NMR (CDCl$_3$) d 172.1, 149.0, 138.2, 136.5, 134.8, 131.6, 127.4, 127.3, 101.5, 40.2, 31.3, 30.9, 28.3, 27.9, 21.2, 19.6, 18.9. LRMS m/z (APCI$^+$) 296 (M+1).

EXAMPLE 37

3-Cyclobutyl-4-(2-trifluoromethyl-phenyl)-2,4,5,7-tetrahydro-pyrazolo[3,4-b]pyridin-6-one 500 MHz $^1$H NMR (CDCl$_3$) d 10.5 (s, 1H), 7.69 (d, J=7.3 Hz, 1H), 7.48 (dd, J=7.8, 7.8 Hz, 1H), 7.37 (dd, J=7.8, 7.8 Hz, 1H), 7.29 (d, J=8.3 Hz, 1H), 4.68 (dd, J=7.3, 7.3 Hz, 1H), 3.12 (dd, J=16.6, 7.8 Hz, 1H), 3.10 (dddd, J=8.1, 8.1, 8.1, 8.1 Hz, 1H), 2.75 (dd, J=16.6, 5.7 Hz, 1H), 2.08-1.76 (m, 6H). LRMS m/z (APCI$^+$) 336 (M+1).

EXAMPLE 38

3-Cyclobutyl-4-(3,4-difluoro-phenyl)-2,4,5,7-tetrahydro-pyrazolo[3,4-b]pyridin-6-one 500 MHz $^1$H NMR (CDCl$_3$) d 10.8 (s, 1H), 7.11 (ddd, J=8.3, 8.3 8.3 Hz, 1H), 6.98 (ddd, J=9.8, 7.8, 2.1 Hz, 1H), 6.92-6.90 (m, 1H), 4.21 (dd, J=7.3, 4.7 Hz, 1H), 3.24 (dddd, J=8.8, 8.8, 8.8, 8.8 Hz, 1H), 3.09 (dd, J=16.1, 7.3 Hz, 1H), 2.79 (dd, J=16.1, 4.7 Hz, 1H), 2.16-2.07 (m, 4H), 1.98-1.81 (m, 2H). 125 MHz $^{13}$C NMR (CDCl$_3$) d 171.6, 151.6, 150.5, 149.7, 148.7, 148.3, 143.5, 140.6, 123.2, 123.1, 117.9, 117.8, 116.3, 116.2, 100.65, 41.2, 34.3, 31.2, 28.3, 19.0. LRMS m/z (APCI$^+$) 304 (M+1).

EXAMPLE 39

N-[4-(3-Cyclobutyl-6-oxo-4,5,6,7-tetrahydro-2H-pyrazolo[3,4-b]pyridin-4-yl)-phenyl]-acetamide 500 MHz $^1$H NMR (DMSO-d$_6$) d 12.0 (s, 1H), 10.3 (s, 1H), 9.89 (s, 1H), 7.46 (d, J=8.3 Hz, 2H), 7.02 (d, J=8.2 Hz, 2H), 4.12 (dd, J=6.7, 4.7 Hz, 1H), 3.17 (dddd, J=8.8, 8.8, 8.8, 8.8 Hz, 1H), 2.81 (dd, J=15.6, 6.7 Hz, 1H), 2.44 (dd, J=16.0, 5.2 Hz, 1H, 2.05-1.90 (m, 4H), 1.80-1.65 (m, 2H). 125 MHz $^{13}$C NMR (DMSO-d$_6$) d 170.1, 168.8, 142.7, 139.5, 138.4, 127.7, 119.8, 101.6, 45.8, 41.6, 34.1, 31.0, 28.8, 28.5, 24.6, 18.7. LRMS m/z (APCI$^+$) 325 (M+1).

EXAMPLE 40

3-Cyclobutyl-4-pyridin-4-yl-2,4,5,7-tetrahydro-pyrazolo[3,4-b]pyridin-6-one

500 MHz $^1$H NMR (CD$_3$OD) d 8.82 (d, J=6.7 Hz, 2H), 8.04 (d, J=6.7 Hz, 2H), 4.73 (dd, J=7.8, 3.1 Hz, 1H), 3.42 (dddd, J=8.8, 8.8, 8.8, 8.8 Hz, 1H), 3.26 (dd, J=16.6, 8.2 Hz, 1H), 2.77 (dd, J=16.6, 3.6 Hz, 1H), 2.15-1.82 (m, 6H). LRMS m/z (APCI$^+$) 269 (M+1).

EXAMPLE 41

5-(3-Cyclobutyl-6-oxo-4,5,6,7-tetrahydro-2H-pyrazolo[3,4-b]pyridin-4-yl)-6-methoxy-3-methyl-1,1a,3,7b-tetrahydro-3-aza-cyclopropa[a]naphthalen-2-one Mixture of isomers obtained, major isomer:
500 MHz $^1$H NMR (CDCl$_3$) d 6.89 (s, 1H), 6.46 (s, 1H), 4.59 (dd, J=7.8, 4.7 Hz, 1H), 3.88 (s, 3H), 3.26 (dddd, J=8.8, 8.8, 8.8, 8.8 Hz, 1H), 3.13 (s, 3H), 3.00 (dd, J=16.6, 4.1 Hz, 1H), 2.84 (dd, J=16.6, 4.1 Hz, 1H), 2.49-2.44 m, 1H), 2.31-2.26 (m, 1H), 2.11-1.27 (m, 7H), 0.62 (dd, J=8.8, 4.1 Hz, 1H). LRMS m/z (APCI$^+$) 393 (M+1).

EXAMPLE 42

3-Cyclobutyl-4-pyridin-3-yl-2,4,5,7-tetrahydro-pyrazolo[3,4-b]pyridin-6-one

500 MHz $^1$H NMR (CDCl$_3$) d 10.9 (s, 1H), 8.53-8.52 (m 2H), 7.49 (ddd, J=7.8, 2.1, 2.1 Hz, 1H), 7.26 (dd, J=8.2, 5.2 Hz, 1H), 4.28 (dd, J=7.2, 5.2 Hz, 1H), 3.20 (dddd, J=8.3, 8.3, 8.3, 8.3 Hz, 1H), 3.13 (dd, J=16.6, 7.8 Hz, 1H), 2.83 (dd, J=16.6, 7.8 Hz, 1H), 2.15-2.03 (m, 4H), 1.95-1.84 (m, 2H). 125 MHz $^{13}$C NMR (DMSO-d$_6$) d 171.6, 149.0, 148.9, 148.8, 143.5, 139.1, 134.9, 124.1, 100.3, 40.9, 32.7, 31.2, 28.3, 19.0. LRMS m/z (APCI$^+$) 269 (M+1).

EXAMPLE 43

3-Cyclobutyl-4-(4-dimethylamino-phenyl)-2,4,5,7-tetrahydro-pyrazolo[3,4-b]pyridin-6-one 500 MHz $^1$H NMR (CD$_3$OD) d 7.68 (d, J=8.3 Hz, 2H), 7.44 (d, J=8.3 Hz, 2H), 4.49 (dd, J=7.3, 4.1 Hz, 1H), 3.31 (s, 6H), 3.39 (dddd, J=8.3, 8.3, 8.3, 8.3 Hz, 1H), 3.13 (dd, J=16.1, 7.3 Hz, 1H), 2.71 (dd, J=16.1, 4.1 Hz, 1H), 2.23-1.81 (m, 6H). LRMS m/z (APCI$^+$) 311 (M+1).

EXAMPLE 44

3-Cyclobutyl-4-(2-dimethylamino-phenyl)-2,4,5,7-tetrahydro-pyrazolo[3,4-b]pyridin-6-one 500 MHz $^1$H NMR (CD$_3$OD) d 7.93 (d, J=8.3 Hz, 1H), 7.63 (d, J=7.3 Hz, 1H), 7.56 (dd, J=7.8, 7.8 Hz, 1H), 7.34 (dd, J=7.8, 7.8 Hz, 1H), 5.00 (dd, J=7.3, masked by H$_2$O Hz, 1H), 3.42 (s, 6H), 3.17-3.10 (m, 2H), 2.73 (dd, J=16.0, 7.3 Hz 1H), 2.20 (dddd, J=9.3, 9.3, 9.3, 9.3 Hz, 1H), 2.07-1.79 (m, 5H). LRMS m/z (APCI$^+$) 311 (M+1).

EXAMPLE 45

3-Cyclobutyl-4-(2-methoxy-pyrimidin-4-yl)-2,4,5,7-tetrahydro-pyrazolo[3,4-b]pyridin-6-one LRMS m/z (APCI$^+$) 310 (M+1).

EXAMPLE 46

3-Cyclobutyl-4-pyridin-2-yl-2,4,5,7-tetrahydro-pyrazolo[3,4-b]pyridin-6-one

500 MHz $^1$H NMR (CD$_3$OD) d 8.83 (d, J=5.7 Hz, 1H), 8.59 ddd, J=7.8, 7.8, 1.6 Hz, 1H), 8.02 (ddd, J=7.2, 7.2, 1.0 Hz, 1H), 7.82 (dd, J=8.3 Hz, 1H), 4.79 (dd, J=7.8, 5.2 Hz, 1H), 3.3-3.24 (m, 2H), 2.85 (dd, J=16.6, 4.7 Hz, 1H), 2.68-1.82 (m, 6H). LRMS m/z (APCI$^+$) 269 (M+1).

EXAMPLE 47

4-(3-Cyclobutyl-6-oxo-4,5,6,7-tetrahydro-2H-pyrazolo[3,4-b]pyridin-4-yl)-piperidine-1-carboxylic acid benzyl ester LRMS m/z (APCI$^+$) 409 (M+1).

EXAMPLE 48

3-Cyclobutyl-4-quinoxalin-2-yl-2,4,5,7-tetrahydro-pyrazolo[3,4-b]pyridin-6-one

500 MHz $^1$H NMR (CDCl$_3$) d 10.8 (s, 1H), 8.74 (s, 1H), 8.08 (dd, J=7.3, 3.6 Hz, 1H), 8.01 (dd, J=6.2, 2.6 Hz, 1H), 7.77-7.42 (m, 2H), 4.62 (bs, 1H), 3.40 (dddd, J=8.8, 8.8, 8.8, 8.8 Hz, 1H), 3.22-3.16 (m, 1H), 2.36-2.09 (m, 4H), 1.86-1.26 (m, 2H). LRMS m/z (APCI$^+$) 320 (M+1).

EXAMPLE 49

3-Cyclobutyl-4-(3,4-dimethyl-phenyl)-2,4,5,7-tetrahydro-pyrazolo[3,4-b]pyridin-6-one 500 MHz $^1$H NMR (CDCl$_3$) d 10.9 (s, 1H), 7.05 (d, J=7.8 Hz, 1H), 6.94 (s, 1H), 6.89 (dd, J=7.8, 1.6 Hz, 1H), 4.15 (dd, J=6.7,6.7 Hz, 1H), 3.19 (dddd, J=8.8, 8.8, 8.8, 8.8 Hz, 1H), 3.04 (dd, J=16.1, 7.2 Hz, 1H), 2.83 (dd, J=16.1, 6.2 Hz, 1H), 2.24 (s, 6H), 2.21-2.03 (m, 4H), 1.90-1.75 (m, 4H). 125 MHz $^{13}$C NMR (CDCl$_3$) d 172.4, 148.2, 143.7, 140.8, 137.1, 135.4, 130.2, 128.6, 124.7, 101.7, 41.4, 34.7, 31.3, 28.4, 28.2, 20.1, 19.6, 18.9. LRMS m/z (APCI$^+$) 296 (M+1).

EXAMPLE 50

3-Cyclobutyl-4-(4-methylsulfanyl-phenyl)-2,4,5,7-tetrahydro-pyrazolo[3,4-b]pyridin-6-one 500 MHz $^1$H NMR (CDCl$_3$) d 10.9 (s, 1H), 7.20 (d, J=8.3 Hz, 2H), 7.09 (d, J=8.3 Hz, 2H), 4.18 (dd, J=6.2, 6.2 Hz, 1H), 3.19 (dddd, J=8.8, 8.8, 8.8 8.8 Hz, 1H), 3.05 (dd, J=16.1, 7.3 Hz, 1H), 2.80 (dd, J=16.1, 5.7 Hz, 1H), 2.48 (s, 3H), 2.18-2.02 (m, 4H), 1.93-1.78 (m, 2H). 125 MHz $^{13}$C NMR (CDCl$_3$) d 172.0, 148.1, 143.9, 140.2, 137.2, 127.8, 127.3, 101.3, 41.2, 34.6, 31.2, 28.4, 28.2, 19.0, 16.1. LRMS m/z (APCI$^+$) 314 (M+1).

EXAMPLE 51

3-Cyclobutyl-4-m-tolyl-2,4,5,7-tetrahydro-pyrazolo[3,4-b]pyridin-6-one

500 MHz $^1$H NMR (CDCl$_3$) d 10.9 (s, 1H), 7.19 (dd, J=7.8, 7.8 Hz, 1H))7.06 (d, J=7.3 Hz, 1H), 6.98 (s, 1H), 6.87 (d, J=masked, 1H), 4.18 (dd, J=6.8, 6.8 Hz, 1H), 4.18 (dddd, J=8.8, 8.8, 8.8, 8.8 Hz, 1H), 3.05 (dd, J=16.6, 7.8 Hz, 1H), 2.84 (dd, J=16.1, 7.8 Hz, 1H), 2.33 (s, 3H), 2.20-2.00 (m, 4H), 1.89-1.78 (m, 2H). 125 MHz $^{13}$C NMR (CDCl$_3$) d 172.1, 148.2, 143.9, 143.3, 138.7, 128.9, 128.0, 124.4, 101.6, 41.2, 35.1, 31.2, 28.4, 28.2, 21.7, 18.9. LRMS m/z (APCI$^+$) 282 (M+1).

EXAMPLE 52

3-Cyclobutyl-4-(2-dimethylamino-4-fluoro-phenyl)-2,4,5,7-tetrahydro-pyrazolo[3,4-b]pyridin-6-one 500 MHz $^1$H NMR (CDCl$_3$) d 10.5 (s, 1H), 7.03 (dd, J=8.3, 6.7 Hz, 2H), 6.93 (dd J=10.4, 2.6 Hz, 2H), 6.76 (ddd, 7.8, 7.8, 2.1 Hz, 1H) 4.80 (dd, J=6.2, 6.2 Hz, 1H), 3.11 (dddd, J=8.8, 8.8, 8.8, 8.8 Hz, 1H), 3.03 (dd, J=16.6, 7.8 Hz, 1H), 2.72 (dd, J=16.6, 6.2 Hz, 1H), 2.69 (s, 6H), 2.16-1.77 (m, 6H). LRMS m/z (APCI$^+$) 329 (M+1).

EXAMPLE 53

3-Cyclobutyl-4-(4-isopropyl-phenyl)-2,4,5,7-tetrahydro-pyrazolo[3,4-b]pyridin-6-one 500 MHz $^1$H NMR (CDCl$_3$) d 10.7 (s, 1H), 7.16 (d, J=8.3 Hz, 1H), 7.08 (d, J=8.3 Hz, 1H), 4.18 (dd, J=6.7, 6.7 Hz, 1H), 3.19 (dddd, J=8.8, 8.8, 8.8, 8.8 Hz, 1H), 3.03 (dd, J=16.6, 6.3 Hz, 1H), 2.92-2.82 (m, 2H), 2.18-2.00 (m, 4H), 1.89-1.80 (m, 2H), 1.24 (d, J=6.7 Hz, 6H). LRMS m/z (APCI$^+$) 310 (M+1).

EXAMPLE 54

3-Cyclobutyl-4-(4-imidazol-1-yl-phenyl)-2,4,5,7-tetrahydro-pyrazolo[3,4-b]pyridin-6-one LRMS m/z (APCI$^+$) 334 (M+1).

EXAMPLE 55

3-Cyclobutyl-4-(2,4-dimethoxy-pyrimidin-5-yl)-2,4,5,7-tetrahydro-pyrazolo[3,4-b]pyridin-6-one 500 MHz $^1$H NMR (CDCl$_3$) d 10.9 (s, 1H), 7.77 (s, 1H), 4.31 (dd, J=7.8, 3.6 Hz, 1H), 4.03 (s, 3H), 3.97 (s, 3H), 3.34 (dddd, J=8.8, 8.8, 8.8, 8.8 Hz, 1H), 3.02 (dd, J=16.6, 7.8 Hz, 1H), 3.02 (dd, J=16.6, 3.6 Hz, 1H), 2.27-2.00 (m, 4H), 1.99-1.84 (m, 2H). 125 MHz $^{13}$C NMR (CDCl$_3$) d 171.8, 168.9, 164.7, 156.3, 148.5, 143.6, 116.2, 98.8, 55.1, 54.3, 38.2, 31.1, 28.1, 28.2, 26.8, 19.1. LRMS m/z (APCI$^+$) 330 (M+1).

EXAMPLE 56

3-Cyclobutyl-4-(2,5-difluoro-phenyl)-2,4,5,7-tetrahydro-pyrazolo[3,4-b]pyridin-6-one 500 MHz $^1$H NMR (CDCl$_3$) d 10.9 (s, 1H), 7.04 (ddd, J=9.3, 9.3, 4.7 Hz, 1H), 6.91 (ddd, J=10.9, 7.3, 3.1 Hz, 1H), 6.67 (ddd, J=9.3, 6.6, 3.6 Hz, 1H), 4.56 (dd, 7.8, 4.1 Hz, 1H), 3.31 (dddd, J=8.8, 8.8, 8.8, 8.8 Hz, 1H), 3.11 (dd, J=16.1, 7.8 Hz, 1H), 2.84 (dd, J=16.6, 4.1 Hz, 1H), 2.2-2.07 (m, 4H), 1.98-1.89 (m, 2H). LRMS m/z (APCI$^+$) 304 (M+1).

EXAMPLE 57

4-(2-Chloro-6-fluoro-phenyl)-3-cyclobutyl-2,4,5,7-tetrahydro-pyrazolo[3,4-b]pyridin-6-one 500 MHz $^1$H NMR (CDCl$_3$) d 11.05 (s, 1H), 7.24-7.18 (m, 2H), 6.98 (dd, J=8.3, 8.3 Hz, 1), 4.95 (dd, J=J=7.8, 7.8 Hz, 1H), 3.10-2.93 (m, 3H), 2.19-1.77 (m, 6H). LRMS m/z (APCI$^+$) 320 (M+1).

EXAMPLE 58

4-(3-Chloro-4-fluoro-phenyl)-3-cyclobutyl-2,4,5,7-tetrahydro-pyrazolo[3,4-b]pyridin-6-one 500 MHz $^1$H NMR (CDCl$_3$) d 10.7 (s, 1H), 7.20 (dd, J=7.3, 2.6 Hz, 1H), 7.09 (dd, J=8.8 Hz, 1H), 7.05-7.02 (m, 1H), 4.19 (dd, J=7.2, 5.2 Hz, 1H), 3.21 (dddd, J=8.8, 8.8, 8.8, 8.8 Hz, 1H), 3.07 (dd, J=16.1, 7.2 Hz, 1H), 2.77 (dd, J=16.1, 5.2 Hz, 1H), 2.16-2.05 (m, 4H), 1.98-1.82 (m, 2H). LRMS m/z (APCI$^+$) 320 (M+1).

EXAMPLE 59

3-Cyclobutyl-4-(2,4,5-trimethyl-phenyl)-2,4,5,7-tetrahydro-pyrazolo[3,4-b]pyridin-6-one 500 MHz $^1$H NMR (CDCl$_3$) d 10.8 (s, 1H), 6.98 (s, 1H), 6.74 (s, 1H), 4.40 (dd, J=7.3, 7.3 Hz, 1H), 3.06 (dddd, J=8.8, 8.8, 8.8, 8.8 Hz, 1H), 2.97 (dd, J=16.6, 7.3 Hz, 1H), 2.71 (dd, J=16.6, 7.8 Hz, 1H), 2.33 (s, 3H), 2.22 (s, 3H), 2.15 (s, 3H), 2.14-2.06 (m, 2H), 2.02-1.96 (m, 2H), 1.86-1.75 (m, 2H). 125 MHz $^{13}$C NMR (CDCl$_3$) d 172.0, 148.3, 144.4, 138.1, 135.3, 134.8, 132.3, 128.4, 101.8, 40.2, 31.2, 30.9, 28.2, 27.9, 19.6, 19.5, 19.0, 18.9. LRMS m/z (APCI$^+$) 310 (M+1).

EXAMPLE 60

3-Cyclobutyl-4-(4-fluoro-phenyl)-2,4,5,7-tetrahydro-pyrazolo[3,4-b]pyridin-6-one 500 MHz $^1$H NMR (CDCl$_3$) d 10.94 (s, 1H), 7.15-7.13 (m, 2H), 7.02-6.98 (m, 2H), 4.21 (bs, 1H), 3.19 (dddd, J=7.8, 7.8, 7.8, 7.8 Hz, 1H) 3.06 (dd, J=16.6, 7.3 Hz, 1H), 2.82-2.78 (m, 1H), 2.18-2.03 (m, 4H), 1.94-1.81 (m, 2H). 125 MHz $^{13}$C NMR (CDCl$_3$) d 171.8, 163.1, 161.1, 148.1, 144.1, 139.0, 128.9, 128.8, 116.0, 115.8, 101.4, 41.3, 34.4, 31.2, 28.3, 28.2 18.9. LRMS m/z (APCI$^+$) 286 (M+1).

EXAMPLE 61

3-Cyclobutyl-4-(2,5-dimethyl-phenyl)-2,4,5,7-tetrahydro-pyrazolo[3,4-b]pyridin-6-one 500 MHz $^1$H NMR (CDCl$_3$) d 10.85 (s, 1H), 7.08 (d, J=7.8 Hz, 1H), 6.96 (d, J=8.3 Hz, 1H), 6.81 (s, 1H), 4.44 (dd, J=7.8, 7.8 Hz, 1H), 3.05 (dddd, J=8.8, 8.8, 8.8, 8.8 Hz, 1H), 2.99 (dd, J=16.1, 7.3 Hz, 1H), 2.72 (dd, J=16.6, 7.8 Hz, 1H), 2.36 (s, 3H), 2.24 (s, 3H), 2.10 (dddd, J=9.3, 9.3, 9.3, 9.3 Hz, 2H), 2.01-1.95 (m, 2H), 1.85-1.77 (m, 2H). 125 MHz $^{13}$C NMR (CDCl$_3$) d 171.9, 148.4, 144.2, 140.7, 136.3, 131.9, 130.8, 127.9, 127.8, 101.5, 40.0, 31.2, 28.2, 28.0, 21.4, 19.2, 18.9. LRMS m/z (APCI$^+$) 296 (M+1).

EXAMPLE 62

3-Cyclobutyl-4-(3-fluoro-2-methyl-phenyl)-2,4,5,7-tetrahydro-pyrazolo[3,4-b]pyridin-6-one 500 MHz $^1$H NMR (CDCl$_3$) d 10.85 (s, 1H), 7.08=7.04 (m, 1H), 6.92 (ddd, J=8.8, 8.8, 8.8 Hz, 1H), 6.76 (dd, J=8.3, 8.3 Hz, 1H), 4.47 (dd, J=6.7, 6.7 Hz, 1H), 3.13-3.00 (m, 2H), 2.74-2.67 (m, 1H), 2.31 (s, 3H), 2.11-2.00 (m, 4H), 1.89-1.78 (m, 2H). LRMS m/z (APCI$^+$) 300 (M+1).

EXAMPLE 63

3-Cyclobutyl-4-(2-methoxy-4-trifluoromethoxy-phenyl)-2,4,5,7-tetrahydro-pyrazolo[3,4-b]pyridin-6-one 500 MHz $^1$H NMR (CDCl$_3$) d 10.64 (s, 1H), 7.10 (dd, J=8.3, 2.0 Hz, 1H), 6.86 (d, J=9.3 Hz, 1H), 6.76 (d, J=2.6 Hz, 1H), 4.51 (dd, J=7.8, 3.6 Hz, 1H), 3.85 (s, 3H), 3.28 (dddd, J=8.8, 8.8, 8.8, 8.8 Hz, 1H), 3.03 (dd, J=16.6, 8.3 Hz, 1H), 2.83 (dd, J=16.6, 3.6 Hz, 1H), 2.05-1.80 (m, 6H). LRMS m/z (APCI$^+$) 382 (M+1).

EXAMPLE 64

4-(5-tert-Butyl-2-methoxy-phenyl)-3-cyclobutyl-2,4,5,7-tetrahydro-pyrazolo[3,4-b]pyridin-6-one LRMS m/z (APCI+) 354 (M+1).

EXAMPLE 65

4-(4-tert-Butyl-phenyl)-3-cyclobutyl-2,4,5,7-tetrahydro-pyrazolo[3,4-b]pyridin-6-one 500 MHz $^1$H NMR (CDCl$_3$) d 10.90 (s, 1H), 7.31-7.25 (m, 2H), 7.09-7.07 (m, 2H), 4.17-4.15 (M, 1H), 3.17-3.15 (m, 1H), 3.05-3.00 (m, 1H), 2.89-2.81 (m, 1H), 2.1402.01 (m, 4H), 1.84-1.81 (m, 2H), 1.29 (bs, 9H). 125 MHz $^{13}$C NMR (CDCl$_3$) d 172.3, 150.1, 148.0, 143.9, 140.1, 126.9, 125.9, 101.8, 41.0, 34.5, 31.6, 31.2, 28.4, 18.9. LRMS m/z (APCI+) 324 (M+1).

EXAMPLE 66

3-(3-Cyclobutyl-6-oxo-4,5,6,7-tetrahydro-2H-pyrazolo[3,4-b]pyridin-4-yl)-benzoic acid methyl ester 500 MHz $^1$H NMR (CDCl$_3$) d 11.05 (s, 1H), 7.94-7.91 (m, 2H), 7.41-7.36 (m, 2H), 4.29 (dd, J=6.7, 6.7 Hz, 1H), 3.92 (s, 3H), 3.14 (dddd, J=8.6, 8.6, 8.6, 8.6 Hz, 1H), 3.09 (dd, J=16.1, 7.3 Hz, 1H), 2.85 (dd, J=16.1, 6.2 Hz, 1H) 2.17-1.96 (m, 4H), 1.89-1.76 (m, 2H). 125 MHz $^{13}$C NMR (CDCl$_3$) d 171.9, 167.2, 148.2, 143.9, 143.7, 131.9, 130.9, 129.3, 128.6, 100.8, 52.5, 41.1, 35.1, 31.2, 28.2, 18.9. LRMS m/z (APCI+) 326 (M+1).

EXAMPLE 67

3-(3-Cyclobutyl-6-oxo-4,5,6,7-tetrahydro-2H-pyrazolo[3,4-b]pyridin-4-yl)-benzonitrile 500 MHz $^1$H NMR (CDCl$_3$) d 11.08 (s, 1H), 7.57-7.54 (m, 1H), 7.46-7.43 (m, 3H), 4.27 (dd, J=7.8, 4.7 Hz, 1H), 3.22 (dddd, J=8.8, 8.8, 8.8, 8.8 Hz, 1H), 3.14 (dd, J=16.1, 7.3 Hz, 1H), 2.81 (dd, J=16.6, 5.2 Hz, 1H), 2.18-2.04 (m, 4H), 1.95-1.82 (m, 2H). 125 MHz $^{13}$C NMR (CDCl$_3$) d 171.4, 148.2, 145.1, 143,8, 131.9, 131.2, 130.9, 130.1, 118.9, 113.6, 100.1, 40.8, 34.6, 31.2, 28.3, 28.2, 19.0. LRMS m/z (APCI+) 293 (M+1).

Preparation 2

2-tert-Butyl-5-cyclobutyl-2H-1pyrazol-3-ylamine

Step A

To 800 mL of THF at −78° C. was added n-BuLi (312.0 mL, 780.0 mmol, 2.5 M in hexanes). After the reaction temperature equilibrated (~15 min), a solution of acetonitrile (40.7 mL, 780.0 mmol in 100 mL of THF) was added dropwise via addition funnel over a 20 min period. The resulting slurry (milky white) was allowed to stir for one hr before a solution of ethyl cyclobutanecarboxylate (53.9 mL, 390.1 mmol in 150 mL of THF) was added down the side of the flask over a 20 min period. After one hr the reaction was warmed to −45° C. (acetonitrile/CO$_2$) and allowed to stir for two hr. The reaction was quenched cold by the dropwise addition of 2 N HCl (~390 mL, pH=7) and then diluted with EtOAc (1 L). The layers were separated and the aqueous layer was extracted with CH$_2$Cl$_2$ (2×600 mL). The combined organic layers were dried over MgSO$_4$, filtered, and concentrated under reduced pressure to yield 3-cyclobutyl-3-oxo-propionitrile (quantitative yield) as a yellow oil that was used without further purification. R$_f$ 0.32 (40% EtOAc/hexanes); m/z (APCI+) 138 (M−1).

Step B

To a slurry of tert-butylhydrazine hydrochloride (68.0 g, 546.1 mmol) in EtOH (1 L) was added NaOH pellets (18.7 g, 468.1 mmol). After 30 min, crude 3-cyclobutyl-3-oxo-propionitrile in EtOH (300 mL) was added. The resulting slurry was heated to 75° C. (oil bath). After 14 hr, the reaction was cooled to room temperature, filtered, and concentrated under reduced pressure. The resulting slurry was taken up in EtOAc and washed with saturated aqueous NaHCO$_3$ solution. The layers were separated and the aqueous layer was extracted with EtOAc. The combined organic layers were dried over MgSO$_4$, filtered through a pad of diatomaceous earth, and concentrated under reduced pressure. Purification of this material was accomplished by recrystallization from 1:1 EtOAc/hexanes to yield, after several crops, the title compound (60.0 g, 80% yield) as a colorless solid. 400 MHz $^1$H NMR (CDCl$_3$) d 5.53 (s, 1H), 3.46 (bs, 2H), 3.42 (dddd, J=8.7, 8.7, 8.7, 8.7 Hz, 1H), 2.32-2.23 (m, 2H), 2.14-1.76 (m, 2H), 1.61 (s, 9H). LRMS m/z (APCI+) 194 (M+1).

Preparation 3

1-tert-Butyl-3-cyclobutyl-4-methyl-1,7-dihydro-pyrazolo[3,4-b]pyridin-6-one

To 2-tert-butyl-5-cyclobutyl-2H-pyrazol-3-ylamine (5.0 g, 25.9 mmol) in acetic acid (25 mL) was added methyl acetoacetate (5.5 mL, 51.8 mmol), and the reaction was heated to 105° C. After 19 hr, the reaction mixture was cooled to room temperature, concentrated to a viscous oil, and then taken up in EtOAc. The reaction mixture was quenched by the slow addition of an aqueous solution of NaHCO$_3$. The layers were separated and the organic layer was dried over MgSO$_4$, filtered, and concentrated under reduced pressure. Purification of this material was accomplished by trituration with hexanes to give, after two crops, the title compound (0.7 g, 52% yield) as a colorless solid. 400 MHz $^1$H NMR (CD$_3$OD) d 6.09 (s, 1H), 3.83 (dddd, J=8.3, 8.3, 8.3, 8.3 Hz, 1H), 2.50-2.27 (m, 7H), 2.08-2.01 (m, 1H), 1.99-1.85 (m, 1H), 1.71 (s, 9H). LRMS m/z (APCI+) 260 (M+1).

EXAMPLE 68

3-Cyclobutyl-4-methyl-2,4,5,7-tetrahydro-pyrazolo[3,4-b]pyridin-6-one-hydrochloride salt Step A To 1-tert-butyl-3-cyclobutyl-4-methyl-1,7-dihydro-pyrazolo[3,4-b]pyridin-6-one (1.0 g, 3.8 mmol) was added TFA (6 mL), and the reaction mixture was heated to 65° C. After five hr, the reaction mixture was cooled to room temperature and concentrated under reduced pressure. The resulting oil was diluted with EtOAc and 9 mL of HCl (1 M in Et$_2$O) was added. The solid was collected and dried under reduced pressure to give 3-cyclobutyl-4-methyl-2,7-dihydro-pyrazolo[3,4-b]pyridin-6-one hydrochloride salt (0.80 mg, 87% yield) as a colorless solid. 400 MHz $^1$H NMR (CD$_3$OD) d 6.48 (s, 1H), 4.14 (dddd, J=8.7, 8.7, 8.7, 8.7 Hz, 1H), 2.67 (s, 3H), 2.55-2.40 (m, 4H), 2.23-2.16 (m, 1H), 2.05-1.95 (m, 1H). LRMS m/z free base (APCI+) 204 (M+1).

Step B

To an aliquot of 3-cyclobutyl-4-methyl-2,7-dihydro-pyrazolo[3,4-b]pyridin-6-one hydrochloride salt (0.20 mg, 0.83 mmol) in MeOH (50 mL) was added 10% Pd/C (100 mg). The reaction mixture was placed in a hydrogenation bottle, pressured with 45 psi $H_2$, and then heated to 60° C. (internal temp). After 12 hr, the reaction was cooled to room temperature, 100 µL of conc. HCl was added, followed by an additional 100 mg of Pd/C. The bottle was re-pressurized with 45 psi $H_2$, and then reheated to 60° C. (internal temp). The reaction mixture was cooled to room temperature after 12 hr, filtered through a plug of diatomaceous earth, and concentrated under pressure. Partial purification of this material was accomplished by MPLC using a 15 g ISCO column (ISCO, Inc., Lincoln, Nebr.), eluting with 2% MeOH/$CH_2Cl_2$ with 0.2% $NH_4OH$. The product-containing fractions were collected and concentrated. This material was re-chromatographed using a 15 g ISCO column, eluting with 4% MeOH/$CH_2Cl_2$ with 0.2% $NH_4OH$. The product-containing fractions were collected and concentrated to afford the title compound (19.0 mg, 11% yield). The monohydrochloride salt was formed using 1M HCl in $Et_2O$. 400 MHz $^1$H NMR ($CD_3OD$) free base d 3.60 (dddd, J=9.5,9.5, 9.5, 0.8 Hz, 1H), 3.10 (dddd, J=10.8, 6.6, 6.6, 6.6, 4.2 Hz, 1H), 2.72 (dd, J=15.8, 6.6 Hz, 1H), 2.36-2.23 (M, 5H), 2.07 (dddd, J=19.9, 9.5, 9.5, 9.5 Hz, 1H), 1.94-1.89 (m, 1H), 1.15 (d, J=7.0 Hz, 3H). LRMS m/z ($APCI^+$) 206 (M+1).

Preparation 4

1-tert-Butyl-3-cyclobutyl-1,7-dihydro-pyrazolo[3,4-b]pyridin-6-one

To 2-tert-butyl-5-cyclobutyl-2H-pyrazol-3-ylamine (5.0 g, 25.9 mmol) in acetic acid (25 mL) was added methyl dimethoxypropionate (7.4 mL, 51.8 mmol), and then the reaction was heated to 110° C. After 24 hr, the reaction mixture was cooled to room temperature, and concentrated to a viscous oil that was diluted with EtOAc. The organic layer was washed with aqueous $NaHCO_3$ and then the organic layer was dried over $MgSO_4$, filtered, and concentrated under reduced pressure. Purification of this material was accomplished by MPLC using a 45 L Biotage® column eluting with 20% EtOAc/hexanes. The product-containing fractions were collected and concentrated under reduced pressure, and the resulting solid was washed with hexanes and dried to afford the title compound (2.0 g, 32% yield) as a colorless solid. $R_f$=0.33 (10% MeOH/$CH_2Cl_2$). 400 MHz $^1$H NMR ($CDCl_3$) d 7.72 (d, J=9.1 Hz, 1H), 6.26 (d, J=9.1 Hz, 1H), 3.68 (dddd, J=8.7, 8.7, 8.7, 8.7 Hz, 1H), 2.46-2.32 (m, 4H), 2.14-1.89 (m, 2H), 1.71 (s, 9H). LRMS m/z ($APCI^+$) 246 (M+1).

EXAMPLE 69

3-Cyclobutyl-2,4,5,7-tetrahydro-pyrazolo[3,4-b]pyridin-6-one

Step A

To 1-tert-butyl-3-cyclobutyl-4-methyl-1,7-dihydro-pyrazolo[3,4-b]pyridin-6-one (1.0 g, 4.1 mmol) was added TFA (6 mL) and the reaction mixture was heated to 65° C. After 12 hr, the reaction was cooled to room temperature and concentrated under reduced pressure. The resulting oil was diluted with EtOAc and 10 mL of HCl (1M in $Et_2O$) was added. The solid was collected and dried under reduced pressure to give 3-cyclobutyl-2,7-dihydro-pyrazolo[3,4-b]pyridin-6-one-hydrochloride salt (0.92 mg, 97% yield) as a colorless solid. HCl salt 400 MHz $^1$H NMR ($CD_3OD$) d 8.36 (d, J=9.1, 1H), 6.60 (d, J=9.1 Hz, 1H), 3.99 (dddd, J=8.7, 8.7, 8.7, 8.7 Hz, 1H), 2.58-2.39 (m, 4H), 2.28-2.14 (m, 1H), 2.08-1.98 (m, 1H). LRMS m/z free base ($APCI^+$) 190 (M+1).

Step B

To an aliquot of 3-cyclobutyl-2,7-dihydro-pyrazolo[3,4-b]pyridin-6-one-hydrochloride salt (0.20 mg, 0.87 mmol) in MeOH (30 mL) was added 10% Pd/C (200 mg). The reaction mixture, in a hydrogenation bottle, was pressured with 45 psi $H_2$, and then the reaction mixture was heated to 65° C. (internal). After 14 hr, the reaction was cooled to room temperature, filtered through a plug of diatomaceous earth, and concentrated under reduced pressure. Partial purification of this material was accomplished by MPLC using a 10 g ISCO column, eluting with 2% MeOH/$CH_2Cl_2$ with 0.2% $NH_4OH$. The product-containing fractions with biproduct were collected and concentrated. This material was further purified by trituration with $Et_2O$. The product was filtered off and dried under reduced pressure to afford the title compound (40.0 mg, 23% yield) as a colorless solid. $R_f$=0.54 (10% MeOH/$CH_2Cl_2$). 400 MHz $^1$H NMR ($CD_3OD$) d 3.54 (dddd, J=8.8, 8.7, 8.7, 8.7 Hz, 1H), 2.75 (apt t, J=7.5 Hz, 2H), 2.58 (apt t, J=7.5 Hz, 2H), 2.33-2.23 (m, 4H), 2.07 (dddd, J=18.7, 9.5, 9.5, 9.5 Hz, 1H), 7.75-7.48 (m, 1H). LRMS m/z ($APCI^+$) 192 (M+1).

EXAMPLE 70

3-Phenyl-2,4,5,7-tetrahydro-pyrazolo[3,4-b]pyridin-6-one

To 3-phenyl-1H-pyrazol-5-amine (0.20 g, 1.26 mmol) in EtOH (5 mL) was added betaine 1-[(6-hydroxy-2,2-dimethyl-4-oxo-4H-1,3-dioxin-5-yl)-methyl]pyridinium hydroxide, inner salt (0.32 g, 1.39 mmol) and then the reaction was heated to 100° C. After 18 hr, the reaction mixture was cooled to room temperature and then place in an ice bath. The product was filtered off and dried under reduced pressure to give the title compound (0.14 g, 53% yield) as a white solid. LRMS m/z ($APCI^+$) 214.

EXAMPLE 71

3-(4-Chloro-phenyl)-2,4,5,7-tetrahydro-pyrazolo[3,4-b]pyridin-6-one

The title compound was prepared in a manner analogous to that described in Example 70 using appropriate starting materials.

LRMS m/z ($APCI^+$) 248 (M+1).

EXAMPLE 72

3,4-Diphenyl-2,4,5,7-tetrahydro-pyrazolo[3,4-b]pyridin-6-one

To 3-phenyl-1H-pyrazol-5-amine (0.20 g, 1.26 mmol) in EtOH (8 mL) was benzaldehyde (0.14 mL, 1.39 mmol) followed by Meldrum's Acid (0.318 g, 1.39 mmol) and then the reaction was heated to 75° C. After 1.5 hr, the reaction mixture was cooled to room temperature and placed in an ice bath. The product was filtered off and dried under reduced pressure to give the title compound (0.26 g, 71% yield) as a white solid. LRMS m/z ($APCI^+$) 290 (M+1).

EXAMPLE 73

3-Phenyl-4-trifluoromethyl-2,4,5,7-tetrahydro-pyrazolo[3,4-b]pyridin-6-one

The title compound was prepared in a manner analogous to that described in Example 72 using appropriate starting materials.
LRMS m/z (APCI$^+$) 282 (M+1).

EXAMPLE 74

4-(2-Chloro-phenyl)-2,4,5,7-tetrahydro-pyrazolo[3,4-b]pyridin-6-one

To a stirring solution of 5-aminopyrazole (2.0 g, 20.1 mmol) in EtOH (40 mL) was added 2-chlorobenzaldehyde (2.8 mL, 20.1 mmol), followed by Meldrum's Acid (2.9 g, 20.1 mmol). The reaction was heated to 65° C. After 16 hr, the reaction was cooled to room temperature, filtered, washed with EtOH, and dried under reduced pressure to give the title compound (3.9 g, 78% yield) as a colorless solid. LRMS m/z (APCI$^+$) 248 (M+1).

Preparation 5

3-(3,3-Dimethoxy-cyclobutyl)-3-oxo-propionitrile

To 200 mL of THF at −78° C. was added n-BuLi (207.0 mL, 517.0 mmol, 2.5 M in hexanes). After the reaction temperature equilibrated (~15 min), a solution of acetonitrile (27.0 mL, 517.0 mmol in 100 mL of THF) was added dropwise via addition funnel over a 20 min period. The resulting milky white slurry was allowed to stir one hr before a solution of 3,3-dimethoxy-cyclobutanecarboxylic acid methyl ester (45.0 g, 258.6 mmol in 150 mL of THF) was added down the side of the flask over a 20 min period. After one hr, the reaction was warmed to −45° C. (acetonitrile/CO$_2$), and allowed to stir for two hr. The reaction was quenched cold by the dropwise addition of 2 N HCl (~260 mL), pH=7 and then diluted with EtOAc (1 L). The layers were separated and the aqueous layer was extracted with CH$_2$Cl$_2$ (2×600 mL). The combined organic layers were dried over MgSO$_4$, filtered, and concentrated under reduced pressure to yield the title compound (quantitative yield) as a yellow oil that was used with out further purification. R$_f$ 0.32 (40% EtOAc/hexanes). m/z (APCI$^+$) 182 (M−1).

Preparation 6

2-tert-Butyl-5-(3,3-dimethoxy-cyclobutyl)-2H-pyrazol-3-ylamine

To a slurry of tert-butylhydrazine hydrochloride (45.1 g, 362.0 mmol) in EtOH (1 L) was added NaOH pellets (12.4 g, 310.3 mmol). After 30 min, crude 3-(3,3-dimethoxy-cyclobutyl)-3-oxo-propionitrile in EtOH (300 mL) was added. The resulting slurry was heated to 75° C. (oil bath). After 14 hr, the reaction was cooled to room temperature, filtered, and concentrated under reduced pressure. Isopropyl ether was added to the resulting slurry. The slurry was stirred for 15 min, filtered, and concentrated to yield a viscous oil. Trituration with ether/hexanes (several crops) gave the title compound (56.2 g, 86% yield over two steps) as a colorless solid: mp 80.9° C. 500 MHz $^1$H NMR (CDCl$_3$) d 5.50 (s, 1H), 3.51 (bs, 2H), 3.18 (s, 3H), 3.16 (s, 3H), 3.19-3.14 (m, 1H), 2.60-2.54 (m, 2H), 2.20-2.14 (m, 2H), 1.59 (s, 9H). LRMS m/z (APCI$^+$) 254 (M+1).

Preparation 7

3-(3-Oxo-cyclobutyl)-4-phenyl-2,4,5,7-tetrahydro-pyrazolo[3,4-b]pyridin-6-one

Step A
To 2-tert-butyl-5-(3,3-dimethoxy-cyclobutyl)-2H-pyrazol-3-ylamine (5.0 g, 25.9 mmol) in EtOH (150 mL) was added benzaldehyde (2.9 mL, 28.5 mmol), followed by Meldrum's Acid (4.1 g (28.5 mmol). The reaction mixture was then heated to 75° C. After two hr, the reaction mixture was cooled to room temperature, and concentrated under reduced pressure. The resulting product was used without further purification.

Step B
To the product of Step A (3-(3,3-dimethoxy-cyclobutyl)-4-phenyl-1,4,5,7-tetrahydro-pyrazolo[3,4-b]pyridin-6-one) in acetone:water 3:1 (100 mL) was added p-toluenesulfonic acid monohydrate (0.98 mg, 5.2 mmol). The resulting reaction mixture was heated to 75° C. After one hr, the reaction was cooled to room temperature and concentrated. The resulting oil was taken up in CH$_2$Cl$_2$, washed with aqueous NaHCO$_3$, dried over MgSO$_4$, and concentrated under reduced pressure to yield a yellow foam. The resulting product was used without further purification.

Step C
To the product of Step B was added neat TFA (60 mL) and then the reaction mixture was heated to 90° C. After 24 hr, the reaction was cooled to room temperature, and concentrated under reduced pressure. The resulting oil was diluted with EtOAc, washed with aqueous 1N NaOH, dried over MgSO$_4$, and concentrated under reduced pressure. Purification of this material was accomplished by MPLC, dry pack using a Biotage® system, eluting with a gradient of 2%, 5%, 10% MeOH/CH$_2$Cl$_2$. The product-containing fractions were collected and concentrated to give the title compound (3.2 g, 45% yield three steps) as a yellow foam. R$_f$=0.45 (10% MeOH/CH$_2$Cl$_2$). 400 MHz $^1$H NMR (CDCl$_3$) d 12.53 (s, 1H), 11.1 (s, 1H), 7.51-7.15 (m, 5H), 4.16 (bs, 1H), 3.16-2.74 (m, 7H). 100 MHz $^{13}$C NMR (CDCl$_3$) d 171.8, 149.1, 142.9, 141.6, 129.3, 127.7, 127.4, 102.9, 77.8, 53.2, 41.1, 35.9, 20.4. LRMS m/z (APCI$^+$) 282 (M+1).

EXAMPLE 76

3-(3-Hydroxy-cyclobutyl)-4-phenyl-2,4,5,7-tetrahydro-pyrazolo[3,4-b]pyridin-6-one To 3-(3-oxo-cyclobutyl)-4-phenyl-2,4,5,7-tetrahydro-pyrazolo[3,4-b]pyridin-6-one (0.91 g, 3.23 mmol) in THF (20 mL) at 0° C. (ice water bath) was added slowly down the side of the flask a solution of LAH (6.4 mL, 1 M hexanes). After one hr, the reaction was quenched with H$_2$O, 15% NaOH, H$_2$O (0.24 □L:0.24 □L:0.71 □L) and then diluted with EtOAc. To this slurry was added 5 g of silica gel and this mixture was concentrated and dried under reduced pressure. Purification of this material was accomplished by MPLC using 40 g ISCO column (dry pack condition), eluting with a gradient of 5%, 10%, 20% MeOH/CH$_2$Cl$_2$. The product-containing fractions were collected and concentrated to give the title compound (0.50 g, 55%) as a colorless solid. R$_f$=0.42 (20% MeOH/CH$_2$Cl$_2$). 400 MHz $^1$H NMR (DMSO-d$_6$) d 11.90 (s, 1H), 10.29 (s, 1H), 7.28-7.23 (m, 2H), 7.20-7.15 (m, 2H), 7.10-7.06 (m, 1H), 5.04 (d, J=6.2 Hz, 1H), 4.16 (dd, J=7.0,4.1 Hz, 1H), 3.86-3.76 (m, 1H), 2.84 (dd, J=15.7, 7.5 Hz, 1H), 2.52 (dddd, J=10.4, 10.4, 7.5, 7.5 Hz, 1H), 2.50-2.48 (dd, J=masked by DMSO, 4.1 Hz, 1H), 2.29-2.12 (m, 2H), 1.89-1.72 (m, 2H). 100 MHz $^{13}$C NMR (DMSO-d$_6$) d 170.0, 149.6, 145.0, 142.2, 129.2, 127.5, 127.2, 101.7, 62.4, 41.4, 34.4, 21.2. LRMS m/z (APCI$^+$) 284 (M+1).

EXAMPLE 77

Benzyl-carbamic acid 3-(6-oxo-4-phenyl-4,5,6,7-tetrahydro-2H-pyrazolo[3,4-b]pyridin-3-yl)-cyclobutyl Ester Step A To a solution of 3-(3-hydroxy-cyclobutyl)-4-phenyl-2,4,5,7-tetrahydro-pyrazolo[3,4-b]pyridin-6-one (0.30 mg, 1.1 mmol) in DMF (3 mL) and EtOAc (5 mL) was added CDI (0.41 mg, 2.54 mmol). The resulting reaction mixture was heated to 75° C. for four hr. The reaction mixture was cooled to room temperature, diluted with EtOAc, washed with H$_2$O (3×10 mL), dried over MgSO$_4$, filtered and concentrated under reduced pressure to give a colorless solid which was used without further purification.

Step B

To the product from Step A in DCE (6 mL) was added DMAP (0.14 g, 1.17 mmol) followed by benzylamine (0.35 mL, 3.18 mmol). The resulting reaction mixture was heated to 75° C. After 14 hr, the reaction was cooled to room temperature, diluted with CH$_2$Cl$_2$, and then washed with aqueous NaHCO$_3$. The organic layer was dried over MgSO$_4$, filtered, and concentrated under reduced pressure. Purification of this material was accomplished by MPLC using a 40 g ISCO column, eluting with a gradient of 1%, 2%, 3%, 5% MeOH/CH$_2$Cl$_2$. The product-containing fractions were collected and concentrated under reduced pressure to give the title compound (0.37 g, 83%) as a colorless solid. R$_f$=0.52 (10% MeOH/CH$_2$Cl$_2$). 400 MHz $^1$H NMR (CD$_3$OD) d 7.34-7.12 (m, 10H), 4.70 (dddd, J=7.5, 7.5, 7.5, 7.5 Hz, 1H), 4.28 (dd, J=7.5, 5.4 Hz, 1H), 4.22 (d, J=6.2 Hz, 2H), 2.99 (dd, 11.6, 7.5 Hz, 1), 2.83 (dddd, J=10.3, 10.4, 7.9, 7.9 Hz, 1H), 2.65 (dd, J=16.2, 5.0 Hz, 1H), 2.52-2.41 (m, 2H), 2.13-2.06 (m, 2H). LRMS m/z (APCI$^+$) 417 (M+1).

Preparation 8

1-tert-Butyl-3-[3-(4-methoxy-benzylamino)-cyclobutyl]-4-phenyl-1,4,5,7-tetrahydro-pyrazolo[3,4-b]pyridin-6-one Step A To 2-tert-butyl-5-(3,3-dimethoxy-cyclobutyl)-2H-pyrazol-3-ylamine (1.0 g, 3.9 mmol) in EtOH (20 mL) was added benzaldehyde (0.44 mL, 4.3 mmol), followed by Meldrum's Acid (0.62 g 4.3 mmol). The reaction mixture was then heated to 75° C. After one hr, the reaction mixture was cooled to 0° C., filtered, and the product dried under reduced pressure. The resulting solid was collected and used without further purification.

Step B

To the product of Step A (3-(3,3-dimethoxy-cyclobutyl)-4-phenyl-1,4,5,7-tetrahydro-pyrazolo[3,4-b]pyridin-6-one) in acetone:water 5:1 (40 mL) was added p-toluenesulfonic acid monohydrate (0.042 mg, 0.20 mmol). The resulting reaction mixture was heated to 75° C. After two hr, the reaction was cooled to room temperature, diluted with CH$_2$Cl$_2$, washed with aqueous NaHCO$_3$, dried over MgSO$_4$, and concentrated under reduced pressure to yield a yellow foam. The resulting product was used without further purification.

Step C

To the product of Step B (1-tert-butyl-3-(3-oxo-cyclobutyl)-4-phenyl-1,4,5,7-tetrahydro-pyrazolo[3,4-b]pyridin-6-one) in THF (25 mL) was added p-methoxybenzylamine. The reaction was fitted with a Dean-Stark trap (containing 4 A molecular sieves) and heated to reflux. After 14 hr, the reaction mixture was cooled to 0° C. and a solution of LAH (9 mL, 1M THF) was added dropwise. After 30 min, the reaction was quenched cold by the successive addition of H$_2$O, 15% NaOH (aq), H$_2$O (0.33 mL, 0.33, mL, 1.0 mL). After 15 min of stirring, MgSO$_4$ was added and the reaction mixture was filtered through a plug of diatomaceous earth, and then concentrated under reduced pressure. Purification of this material was accomplished by MPLC, using 35 g ISCO column, eluting with a 10% MeOH/CH$_2$Cl$_2$. The product-containing fractions were collected and concentrated to give the title compound as a light yellow foam. R$_f$=0.38 (10% MeOH/CH$_2$Cl$_2$). LRMS m/z (APCI$^+$) 459 (M+1).

EXAMPLE 78

2-(3,4-Dichloro-phenyl)-N-[3-(6-oxo-4-phenyl-4,5,6,7-tetrahydro-2H-pyrazolor3,4-b]pyridin-3-yl)-cyclobutyl]-acetamide Step A To 1-tert-butyl-3-[3-(4-methoxy-benzylamino)-cyclobutyl]-4-phenyl-1,4,5,7-tetrahydro-pyrazolo[3,4-b]pyridin-6-one (0.10 g, 0.22 mmol) in EtOAc (4 mL) was added 3,4-dichlorophenylacetic acid (0.13 g, 0.44 mmol), followed by a solution of 1-propanephosphonic acid cyclic anhydride (280 mL, 50 wt % solution in EtOAc). After 16 hr, the reaction was quenched with aqueous 1N NaOH. The reaction mixture was diluted with EtOAc, and the layers were separated. The organic layer was washed with aqueous 1N NaOH, brine, dried over MgSO$_4$, filtered, and then concentrated under reduced pressure. This material was used further without purification. LRMS m/z (APCI$^+$) 645 (M+1).

Step B

To the product of Step A was added neat TFA and the resulting mixture was heated to 65° C. After 24 hr, the reaction was cooled to room temperature, and concentrated under reduced pressure. The resulting oil was diluted with EtOAc, and washed with aqueous NaHCO$_3$. The organic layer was dried over MgSO$_4$, filtered, and concentrated under reduced pressure. Purification of this material was accomplished by MPLC using a 10 g ISCO column, eluting with a gradient of 2% to 10% MeOH. The product-containing fractions were collected and concentrated to give the title compound (37 mg, 36% yield over two steps) as a yellow solid. R$_f$=0.38 (10% MeOH/CH$_2$Cl$_2$). 400 MHz $^1$H NMR (DMSO-d$_6$) d 11.9 (s, 1H), 10.3 (s, 1H), 8.22 (d, J=7.5 Hz, 1H), 7.53 (d, J=8.3 Hz, 1H), 7.46 (d, J=2.1 Hz, 1H), 7.28-7.24 (m, 2H), 7.20-7.16 (m, 2H), 7.10-7.08 (m, 2H), 4.19 (dd, J=6.6, 4.2 Hz, 1H), 3.92 (dddd, J=16.2, 8.7, 8.7, 8.7 Hz, 1H), 3.35 (s, 2H), 2.88-2.76 (m, 2H), 2.45 center of outer d (dd, J=DMSO masked, 4.6 Hz, 1H), 2.27-2.21 (m, 2H), 1.87 (app dq's, J=10.4H). LRMS m/z (APCI$^+$) 469 (M+1).

EXAMPLE 79

N-[3-(6-Oxo-4-phenyl-4,5,6,7-tetrahydro-2H-pyrazolo[3,4-b]pyridin-3-yl)-cyclobutyl]-acetamide Step A To a solution of 1-tert-butyl-3-[3-(4-methoxy-benzylamino)-cyclobutyl]-4-phenyl-1,4,5,7-tetrahydro-pyrazolo [3,4-b]pyridin-6-one (0.10 g, 0.22 mmol) in $CH_2Cl_2$ (4 mL) was added triethylamine (excess), followed by acetic anhydride (excess). After 16 hr, the reaction was concentrated under reduced pressure. This material was used further without purification. LRMS m/z (APCI$^+$) 325 (M+1).

Step B

To the product of Step A was added neat TFA and the resulting mixture was heated to 65° C. After 24 hr, the reaction was cooled to room temperature, and concentrated under reduced pressure. The resulting oil was diluted with EtOAc, and washed with aqueous $NaHCO_3$. The organic layer was dried over $MgSO_4$, filtered, and concentrated under reduced pressure. Purification of this material was accomplished by MPLC using a 10 g ISCO column, eluting with a gradient of 2%, 10% MeOH. The product-containing fractions were collected and concentrated to give the title compound (30 mg, 42% yield over two steps) as a light yellow solid. 400 MHz $^1$H NMR (DMSO-$d_6$) d 11.9 (s, 1H), 10.3 (s, 1H), 7.95 (d, J=7.5 Hz, 1H), 7.29-7.25 (m, 2H), 7.20-7.17 (m, 1H), 7.11-7.09 (m, 2H), 4.20 (dd, J=7.1, 4.2 Hz, 1H), 3.93 (dddd, J=14.9, 7.5, 7.5, 7.5 Hz, 1H), 2.87-2.74 (m, 2H), 2.44 center outer d (dd, J=DMSO masked, 4.5 Hz, 1H), 2.24-2.18 (m, 2H), 1.97-1.77 (m, 2H), 1.71 (s, 3H). LRMS m/z (APCI$^+$) 325 (M+1).

EXAMPLE 80

2-(2-Chloro-phenoxy)-N-[3-(6-oxo-4-trifluoromethyl-4,5,6,7-tetrahydro-2H-pyrazolo[3,4-b]pyridin-3-yl)-cyclobutyl]-acetamide The title compound was prepared in a manner analogous to that described in Example 78 using appropriate starting materials.

500 MHz $^1$H NMR (DMSO-$d_6$) d 12.2 (s, 1H), 10.4 (s, 1H), 8.05 (d, J=7.9 Hz, 1H), 7.44 (dd, J=7.9, 1.7 Hz, 1H), 7.28 (ddd, J=8.3, 1.7 1.7 Hz, 1H), 7.04 (dd, J=8.3, 1.2 Hz, 1H), 6.98 (ddd, J=7.5, 7.5, 1.3 Hz, 1H), 4.57 (s, 2H), 4.25 (dddd, J=8.3, 8.3, 8.3, 8.3, 1H), 3.86 (dddd, J=9.1, 9.1, 9.1, 9.1 Hz, 1H), 3.19 (dddd, J=10.4, 10.4, 10.4,10.4 Hz, 1H), 2.92 (dd, J=17.0, 8.3 Hz, 1H), 2.59-2.43 (m, 3H), 2.25-2.08 (m, 2H). LRMS m/z (APCI$^+$) 443 (M+1).

Preparation 9

1-tert-Butyl-3-(3-oxo-cyclobutyl)-4-(2,4,5-trifluoro-phenyl)-1,4,5,7-tetrahydro-pyrazolo[3,4-b]pyridin-6-one Step A To a stirring solution of 2-tert-butyl-5-(3,3-dimethoxy-cyclobutyl)-2H-pyrazol-3-ylamine, (6.6 g, 26.2 mmol) in 75 mL of ethanol was added 2,4,5-trifluorobenzaldehyde (3.0 mL, 26.2 mmol) followed by Meldrum's Acid (3.8 g, 26.2 mmol), and then the reaction mixture was heated to 75° C. After three hr, the reaction was cooled to room temperature, and concentrated under reduced pressure. The crude material was used without purification.

Step B

The product of Step A was taken up in 75 mL of acetone/water (3:1). To this stirring solution was added p-toluenesulfonic acid monohydrate (1.0 g, 5.3 mmol), and the reaction mixture was heated to 75° C. (oil bath). After two hr, the reaction was cooled to room temperature, and concentrated. The residue was taken up in $CH_2Cl_2$, and washed with brine. The layers were separated and the organic layer was dried over $MgSO_4$, filtered, and concentrated under reduced pressure. Purification of this material was accomplished by washing the resulting solid with isopropyl ether. The product was collected and dried under reduced pressure to yield the title compound (6.9 g, 67% yield) as a tan solid. LRMS m/z (APCI$^+$) 392 (M+1).

Preparation 10

3-{3-[1-tert-Butyl-6-oxo-4-(2,4,5-trifluoro-phenyl)-4,5,6,7-tetrahydro-1H-pyrazolo[3,4-b]pyridin-3-yl]-1-hydroxy-cyclobutyl}-benzonitrile To a stirring solution of 3-bromobenzonitrile (3.7 g, 20.4 mmol) in 50 mL of THF at −78° C. (acetone/$CO_2$ bath) was added a solution of n-BuLi (8.2 mL, 20.4 mmol, 2.5 M in hexanes). After 15 min, a solution of 1-tert-butyl-3-(3-oxo-cyclobutyl)-4-(2,4,5-trifluoro-phenyl)-1,4,5,7-tetrahydro-pyrazolo[3,4-b]pyridin-6-one (2.0 g, 5.1 mmol in 10 mL of THF) was added. After one hr, the reaction mixture was quenched cold by the addition of a saturated $NH_4Cl$ solution, and was then allowed to warm to room temperature. The reaction mixture was diluted with $CH_2Cl_2$, and the layers were separated. The organic layer was dried over $MgSO_4$, filtered through a pad of diatomaceous earth, and concentrated under reduced pressure to give a tan solid. Purification of this material was accomplished by MPLC using a 35 g ISCO cartridge on a Biotage® system eluting with a gradient of 25-50% EtOAc/hexanes. The product-containing fractions were collected and concentrated to yield the title compound (0.98 g, 40% yield) as a tan solid. R$_f$=0.29 (50% EtOAc/hexanes).

EXAMPLE 81

3-{3-[6-Oxo-4-(2,4,5-trifluoro-phenyl)-4,5,6,7-tetrahydro-2H-pyrazolo[3,4-b]pyridin-3-yl]-cyclobutyl}-benzonitrile Step A To 3-{3-[1-tert-butyl-6-oxo-4-(2,4,5-trifluoro-phenyl)-4,5,6,7-tetrahydro-1H-pyrazolo[3,4-b]pyridin-3-yl]-1-hydroxy-cyclobutyl}-benzonitrile was added neat trilfuoroacetic acid (15 mL), and the reaction was heated to 75° C. After 14 hr, the reaction was cooled to room temperature, and then concentrated under reduced pressure. The resulting material was used without further purification.

Step B

To the product of Step A in EtOH (50 mL) was added Pd/C (200 mg) and then the reaction was pressurized in a hydrogenation bottle with $H_2$ (45 psi). After 5 hr, the reaction was filtered through a plug of diatomaceous earth, and concentrated under reduced pressure. The residue was taken up in EtOAc and washed with aqueous NaOH (1M). The organic layer was dried over $MgSO_4$, silica gel was added (dry pack) and concentrated under reduced pressure. Purification of this material was accomplished by MPLC (dry pack) using a Biotage® column, eluting with a gradient of 2%, 5% MeOH/CH$_2$Cl$_2$. The product-containing fractions were collected and concentrated under reduced pressure. Further purification was accomplished by washing the resulting solid with isopropyl ether to yield the title compound (0.23 g, 28%) as a colorless solid. 500 MHz $^1$H NMR (DMSO-d$_6$) d 12.2 (s, 1H), 10.4 (s, 1H), 7.74 (s, 1H), 7.66 (ddd, 7.5, 1.3, 1.3 Hz, 1H), 7.58-7.52 (m, 3H), 6.93 (ddd, J=7.5, 1.2, 1.2 Hz, 1H), 4.46 (dd, 7.5, 5.0 Hz, 1H), 3.37-3.28 (m, 1H), 3.16-3.06 (m, 1H), 2.89 (dd, J=16.2, 7.5 Hz, 1H), 2.45-2.43 (m, 1H), 2.35-2.27 (m 1H), 2.24-2.06 (m, 2H). LRMS m/z (APCI$^+$) 423 (M+1)

EXAMPLE 82

3-{3-[6-Oxo-4-(2,4,5-trifluoro-phenyl)-4,5,6,7-tetrahydro-2H-pyrazolo[3,4-b]pyridin-3-yl]-cyclobutyl}-benzaldehyde To 3-{3-[6-oxo-4-(2,4,5-trifluoro-phenyl)-4,5,6,7-tetrahydro-2H-pyrazolo[3,4-b]pyridin-3-yl]-cyclobutyl}-benzonitrile (0.16 g, 0.34 mmol) in CHCl$_3$ (5 mL) at −78° C. (acetone/CO$_2$ bath) was added a solution of DIBAL-H (1.8 mL, 1M in CH$_2$Cl$_2$). After 30 min, the reaction was quenched cold with MeOH (1 mL), followed by a saturated aqueous solution of sodium and potassium tartrates. The reaction mixture was allowed to warm to room temperature and stirred for one hr. The reaction mixture was extracted with CHCl$_3$, and the combined organic layers were dried over MgSO$_4$. The organic layer was filtered, and concentrated under reduced pressure. Purification of this material was accomplished by MPLC using a 10 g ISCO column, eluting with 4% MeOH/CHCl$_3$. The product-containing fractions were collected and concentrated to give the title compound. LRMS m/z (APCI$^+$) 426 (M+1)

EXAMPLE 83

3-[3-(3-Hydroxymethyl-phenyl)-cyclobutyl]-4-(2,4,5-trifluoro-phenyl)-2,4,5,7-tetrahydro-pyrazolo[3,4-b]pyridin-6-one To 3-{3-[6-oxo-4-(2,4,5-trifluoro-phenyl)-4,5,6,7-tetrahydro-2H-pyrazolo[3,4-b]pyridin-3-yl]-cyclobutyl}-benzaldehyde (15 mg, 0.03 mmol) in THF:MeOH (3 mL 3:1) was added sodium borohydride (10 mg, 0.26 mmol). After 30 min, the reaction was quenched by the addition of 5 drops of aqueous NaOH (1N). The reaction mixture was concentrated under reduced pressure. Purification of this material was accomplished by preparative plated chromatography. The product band was collected, extracted with EtOAc, filtered, and concentrated to give the title compound. LRMS m/z (APCI$^+$) 428 (M+1).

EXAMPLE 84

3-(3-{3-[(Cyclopropylmethyl-amino)-methyl]-phenyl}-cyclobutyl)-4-(2,4,5-trifluoro-phenyl)-2,4,5,7-tetrahydro-pyrazolo[3,4b]pyridin-6-one To 3-{3-[6-oxo-4-(2,4,5-trifluoro-phenyl)-4,5,6,7-tetrahydro-2H-pyrazolo[3,4-b]pyridin-3-yl]-cyclobutyl}-benzaldehyde (68 mg, 0.16 mmol) in THF was added 4 A molecular sieves (100 mg) followed by aminomethylcyclopropane (0.37 mg, 5.2 mmol), and then the reaction mixture was heated to 75° C. (oil bath). After two hr, the reaction was cooled to room temperature and NaCNBH$_3$ (0.10 g, 1.6 mmol) was added. After 20 min, MeOH (1 mL) was added, and the reaction mixture was concentrated. Purification of this material was accomplished by preparative plated chromatography. The product band was collected, extracted with EtOAc, filtered, and concentrated to give the title compound. LRMS m/z (APCI$^+$) 481 (M+1).

EXAMPLE 85

3-[3-(6-Oxo-4,5,6,7-tetrahydro-2H-pyrazolo[3,4-b]pyridinyl-cyclobutyl]-benzonitrile The title compound was prepared in a manner analogous to that described in Example 81 using appropriate starting materials.
400 MHz $^1$H NMR (CD$_3$OD) d 7.21 (ddd, J=10.8, 7.9, 3.7 Hz, 2H), 7.15 (dd, J=2.0 Hz, 1H), 7.14 (s, 1H), 7.02 (d, J=7.5 Hz, 1H), 6.80 (ddd, J=10.9, 8.7, 7.0 Hz, 1H), 4.61 (dd, J=7.5, 3.7 Hz, 1H), 4.56 (s, 2H), 3.41 (dddd, J=17,8, 7.9 Hz, 1H), 3.05 (dd, J=16.2, 7.5 Hz, 1H), 2.63 (dd, J=16.2, 3.7 Hz, 1H), 2.2.57-2.45 (m, 2H), 2.18 (ddd, J=20.3, 10.0, 2.9 Hz, 2H). LRMS m/z (APCI$^+$) 293 (M+1).

EXAMPLE 86

3-[3-(3-Hydroxymethyl-phenyl)-cyclobutyl]-2,4,5,7-tetrahydro-pyrazolo[3,4-b]pyridin-6-one The title compound was prepared in a manner analogous to that described in Example 83 using appropriate starting materials.
400 MHz $^1$H NMR (CD$_3$OD) d 7.29-7.25 (m, 2H), 7.18-7.16 (m, 2H), 4.59 (s, 2H), 3.52 (dddd, J=18.2, 15.3, 10.8, 7.9 Hz, 2H), 2.79-2.69 (m, 4H), 2.60-2.56 (m, 2H), 2.38-2.30 (m, 2H). LRMS m/z (APCI$^+$) 298 (M+1).

EXAMPLE 87

3-[3-(3-Hydroxymethyl-phenyl)-cyclobutyl]-4-trifluoromethyl-2,4,5,7-tetrahydro-pyrazolo[3,4-b]pyridin-6-one The title compound was prepared in a manner analogous to that described in Example 83 using appropriate starting materials.
LRMS m/z (APCI$^+$) 366 (M+1).

Preparation 11

N-[2-tert-Butyl-5-(3,3-dimethoxy-cyclobutyl)-2H-pyrazol-3-yl]-2,2,2-trifluoro-acetamide To a stirring solution of 2-tert-butyl-5-(3,3-dimethoxy-cyclobutyl)-2H-pyrazol-3-ylamine (5.0 g, 19.7 mmol) in EtOAc (40 mL) was added triethylamine (27 mL, 197 mmol), TFA (2.3 mL, 29.6 mmol), followed by a solution of 1-propanephosphonic acid cyclic anhydride (25 mL, 50 wt % sol. in EtOAc, 39.4 mmol). After 72 hr, the reaction was diluted with EtOAc and washed with aqueous NaOH (1 N). The organic layer was dried over MgSO$_4$, filtered, and concentrated under reduced pressure. Purification of this material was accomplished by MPLC, using a Biotage® column (35 L), eluting with 25% EtOAc/hexanes. The product-containing fractions were collected and concentrated to yield the title compound (4.1 g, 60% yield) as a colorless oil. 400 MHz $^1$H NMR (CDCl$_3$) d 8.00 (bs, 1H), 6.26 (s, 1H), 3.22 (dddd, J=8.7, 8.7, 8.7, 8.7, Hz, 1H), 3.18

(s, 3H), 3.15 (s, 3H), 2.61-2.55 (m, 2H), 2.25-2.19 (m, 2H), 1.59 (s, 9H). LRMS m/z (APCI$^+$) 350 (M+1).

Preparation 12

N-[2-tert-Butyl-5-(3-oxo-cyclobutyl)-2H-pyrazol-3-yl]-2,2,2-trifluoro-acetamide

To a stirring solution of N-[2-tert-butyl-5-(3,3-dimethoxy-cyclobutyl)-2H-pyrazol-3-yl]-2,2,2-trifluoro-acetamide (6.5 g, 18.5 mmol) in acetone (182 mL) and water (61 mL) was added p-toluenesulfonic acid monohydrate (1.8 g, 9.5 mmol) and the reaction mixture was heated to 65° C. After 1.5 hr, the reaction mixture was cooled to room temperature, diluted with $CH_2Cl_2$ (250 mL), and water (50 mL). The layers were separated and the aqueous layer was back-extracted with $CH_2Cl_2$. The combined organic layers were dried over $MgSO_4$, filtered, and concentrated under reduced pressure. Purification of the resulting material was accomplished by trituration with isopropyl ether. The product was collected and dried under reduced pressure to yield the title compound (4.2 g, 76% yield, two crops) as a yellow solid. 400 MHz $^1$H NMR (CDCl$_3$) d 7.86 (bs, 1H), 6.33 (s, 1H), 3.62 (dddd, J=7.6, 7.6, 7.6, 7.6 Hz, 1H), 3.46-3.30 (m, 4H), 1.62 (s, 9H). LRMS m/z (APCI$^+$) 304 (M+1).

Preparation 13

N-{2-tert-Butyl-5-[3-(3-cyano-phenyl)-3-hydroxy-cyclobutyl]-2H-pyrazol-3-yl}-2,2,2-trifluoro-acetamide To a stirring solution of 3-bromobenzonitrile (12.6 g, 69.0 mmol) in 245 mL of THF at −78° C. (acetone/CO$_2$ bath) was added a solution of n-BuLi (27.6 ml, 69 mmol, 2.5 M in hexanes). After 15 min, a solution of N-[2-tert-butyl-5-(3-oxo-cyclobutyl)-2H-pyrazol-3-yl]-2,2,2-trifluoro-acetamide (4.0 g, 11.5 mmol in 200 mL of THF) was added. After one hr, the reaction mixture was quenched cold by the addition of a saturated NH$_4$Cl solution, and was then allowed to warm to room temperature. The reaction mixture was diluted with EtOAc, and the layers were separated. The organic layer was washed with brine, dried over MgSO$_4$, filtered through a pad of diatomaceous earth, and concentrated under reduced pressure. Purification of this material was accomplished by MPLC using a Biotage® column, eluting with 25% EtOAc/hexanes. The product-containing fractions were collected and concentrated to yield the title compound (4.6 g, 98% yield). LRMS m/z (APCI$^+$) 407 (M+1).

Preparation 14

N-{2-tert-Butyl-5-[3-(3-cyano-phenyl)-cyclobutyl]-2H-pyrazol-3-yl}-2,2,2-trifluoro-acetamide Step A To N-{2-tert-butyl-5-[3-(3-cyano-phenyl)-3-hydroxy-cyclobutyl]-2H-pyrazol-3-yl}-2,2,2-trifluoro-acetamide (4.6 g, 11.3 mmol) in CH$_2$Cl$_2$ (113 mL) was added methanesulfonic acid (7.33 mL, 113 mmol). The resulting mixture was heated to 45° C. After one hr, the reaction mixture was cooled to room temperature and concentrated to a solid that was used without further purification.

Step B

To the product of Step A in EtOH (113 mL) was added pyridine (9.1 mL, 113 mmol) followed by 10% Pd/C (1.1 g). The reaction mixture was pressurized in a hydrogenation bottle with 45 psi H$_2$. After one hr, the reaction mixture was purged with N$_2$, filtered through a plug of celite, and concentrated under reduced pressure. This material was taken up in EtOAc and washed with a saturated aqueous solution of NaHCO$_3$. The organic layer was dried over MgSO$_4$, filtered, and concentrated under reduced pressure to yield the title compound (4.1 g, 93%) as a yellow foam. This material was used without further purification. LRMS m/z (APCI$^+$) 391 (M+1).

Preaparation 15

N-{2-tert-Butyl-5-[3-(3-formyl-phenyl)-cyclobutyl]-2H-pyrazol-3-yl}-2,2,2-trifluoro-acetamide To N-{2-tert-butyl-5-[3-(3-cyano-phenyl)-cyclobutyl]-2H-pyrazol-3-yl}-2,2,2-trifluoro-acetamide (4.0 g, 10.2 mmol) in CH$_2$Cl$_2$ (50 mL) at 0° C. (ice/water bath) was added a solution of DIBAl-H (25 mL, 1 M in CH$_2$Cl$_2$). After 20 min, the reaction was quenched with MeOH, followed by an aqueous solution of Rochelle's Salts. This mixture was poured into a flask containing 800 mL of CH$_2$Cl$_2$, and stirred overnight. The layers were separated and the organic layer was dried over MgSO$_4$, filtered, and concentrated under reduced pressure. Purification of this material was accomplished by MPLC using a Biotage column, eluting with a gradient of 10-25% EtOAc. The product-containing fractions were collected and concentrated to give the title compound (0.49 g, 12%). LRMS m/z (APCI$^+$) 394 (M+1).

Preparation 16

N-{2-tert-Butyl-5-[3-(3-cyclopropylaminomethyl-phenyl)-cyclobutyl]-2H-pyrazol-3-yl}-2,2,2-trifluoro-acetamide Hydrochloride To a stirring solution of N-{2-tert-butyl-5-[3-(3-formyl-phenyl)-cyclobutyl]-2H-pyrazol-3-yl}-2,2,2-trifluoro-acetamide (0.49 g, 1.25 mmol) in CH$_2$Cl$_2$ (13 mL) was added acetic acid (86 uL, 1.5 mmol), followed by cyclopropylamine (103 uL, 1.5 mmol). After 30 min, sodium triacetoxyborohydride (0.53 g, 2.5 mmol) was added. The reaction was quenched after four hr. with a saturated solution of NaHCO$_3$. The aqueous layer was extracted with CH$_2$Cl$_2$, and the combined organic layers were dried over MgSO$_4$, filtered, and concentrated under reduced pressure. Formation of the hydrochloride salt was accomplished using 2M HCl in Et$_2$O to give the title compound (0.53 g). This material was used without further purification.

LRMS m/z (APCI$^+$) 435 (M+1).

Preparation 17

5-[3-(3-Cyclopropylaminomethyl-phenyl)-cyclobutyl]-1H-pyrazol-3-ylamine

Step A

To N-{2-tert-butyl-5-[3-(3-cyclopropylaminomethyl-phenyl)-cyclobutyl]-2H-pyrazol-3-yl}-2,2,2-trifluoro-acetamide hydrochloride (0.53 g, 1.1 mmol) was added neat TFA (11 mL) and the reaction was heated to 65° C. After complete consumption of starting material, as determined by LRMS, the reaction was cooled to room temperature and concentrated under reduced pressure. This material was process further without purification.

Step B

To the product of Step A was added a methanolic solution of ammonia (10 mL, 2M MeOH). After 16 hr, an additional amount of a methanolic solution of ammonia (3 mL, 2M MeOH) was added. After a total of 40 hr, the reaction mixture was concentrated under reduced pressure. Purification of this material was accomplished by MPLC, using a 35 g ISCO column, eluting with a gradient of 5-15% MeOH/ CH$_2$Cl$_2$ The product-containing fractions were collected and concentrated to give the title compound (0.43 g, quantitative yield). 400 MHz $^1$H NMR (CD$_3$OD) d 7.40-7.31 (m, 4H), 4.28 (s, 2H), 3.63-3.45 (m, 2H), 2.81-2.70 (m, 3H), 2.33-2.24 (m, 2H), 0.93-0.76 (m, 4H). LRMS m/z (APCI$^+$) 283 (M+1).

EXAMPLE 88

3-[3-(3-Cyclopropylaminomethyl-phenyl)-cyclobutyl]-4-isopropyl-2,4,5,7-tetrahydro-pyrazolo[3,4-b]pyridin-6-one trifluoroacetic acid salt To 2-methyl-propionaldehyde (8.0 mg, 0.11 mmol) was added a solution of 5-[3-(3-cyclopropylaminomethyl-phenyl)-cyclobutyl]-1H-pyrazol-3-ylamine (0.22 mL, 0.11 mmol, 0.5 M in MeOH) followed by a solution of Meldrum's Acid (0.11 mL, 0.11 mmol, 1 M CH$_2$Cl$_2$) and then the reaction was heated to 65° C. After one hr, the reaction mixture was cooled to room temperature, and concentrated. Purification of the resulting material was accomplished by HPLC, with a gradient of acetonitrile/H$_2$O with 0.01% trifluoroacetic acid. The product was collected and concentrated to give the title compound. 500 MHz $^1$H NMR (CD$_3$OD) d 7.45-7.40 (m, 3H), 7.35-7.34 (m, 1H), 4.31 (s, 2H), 3.64-3.54 (m, 2H), 2.86-2.58 (m, 6H), 2.46-2.50 (m, 2H), 1.80-1.74 (m 1H), 0.96-0.40 (m, 10H). LRMS m/z (APCI$^+$) 379 (M+1).

EXAMPLE 89

3-[3-(3-Cyclopropylaminomethyl-phenyl)-cyclobutyl]-4-ethyl-2,4,5,7-tetrahydro-pyrazolo[3,4-b]pyridin-6-one The title compound was prepared in a manner analogous to that described in Example 88 using appropriate starting materials.

500 MHz $^1$H NMR (CD$_3$OD) d 7.45-7.40 (m, 3H), 7.36-7.33 (m, 1H), 4.32 (s, 2H), 3.63-3.56 (m, 2H), 2.98-2.90 (m, 1H), 2.81-1.71 (m, 4H), 2.49 (dd, J=16.1, 2.3 Hz, 1H), 2.48-2.33 (m, 2H), 1.56-1.49 (m, 2H), 0.95-0.86 (m, 7H). LRMS m/z (APCI$^+$) 365 (M+1).

EXAMPLE 90

3-[3-(3-Cyclopropylaminomethyl-phenyl)-cyclobutyl]-4-isobutyl-2,4,5,7-tetrahydro-pyrazolo[3,4-b]pyridin-6-one The title compound was prepared in a manner analogous to that described in Example 88 using appropriate starting materials.

500 MHz $^1$H NMR (CD$_3$OD) d 7.45-7.42 (m, 3H), 7.36-7.34 (m, 1H), 4.31 (s, 2H), 3.64-3.54 (m, 2H), 3.06 (dddd, J=8.8, 8.8, 2.1, 0.0 Hz, 1H), 2.82-2.76 (m, 3H), 2.73 (dd, J=16.1, 6.7 Hz, 1H), 2.48 (dd, J=16.1, 2.6 Hz, 1H), 2.42-2.34 (m, 2H), 1.61-1.57 (m, 1H), 1.36-1.27 (m, 2H), 1.00-0.87 (m, 10H). LRMS m/z (APCI$^{30}$ ) 393 (M+1).

EXAMPLE 91

4-Cyclohexyl-3-[3-(3-cyclopropylaminomethyl-phenyl)-cyclobutyl]-2,4,5,7-tetrahydro-pyrazolo[3,4-b]pyridin-6-one The title compound was prepared in a manner analogous to that described in Example 88 using appropriate starting materials.

500 MHz $^1$H NMR (CD$_3$OD) d 7.46-7.43 (m, 3H), 7.35-7.33 (m, 1H), 4.31 (s, 2H), 3.62-3.54 (m, 2H), 2.82-2.74 (m, 4H), 2.68-2.60 (m, 2H), 2.44-2.32 (m, 2H), 1.80-0.03 (m, 15H). LRMS m/z (APCI$^+$) 419 (M+1).

EXAMPLE 92

4-Cyclohex-3-enyl-3-[3-(3-cyclopropylaminomethyl-phenyl)-cyclobutyl]-2,4,5,7-tetrahydro-pyrazolo[3,4-b]pyridin-6-one The title compound was prepared in a manner analogous to that described in Example 88 using appropriate starting materials.

LRMS m/z (APCI$^+$) 417 (M+1).

EXAMPLE 93

3-[3-(3-Cyclopropylaminomethyl-phenyl)-cyclobutyl]-4-p-tolyl-2,4,5,7-tetrahydro-pyrazolo[3,4-b]pyridin-6-one The title compound was prepared in a manner analogous to that described in Example 88 using appropriate starting materials.

500 MHz $^1$H NMR (CD$_3$OD) d 7.38 (dd, J=7.3, 7.3 Hz, 1H), 7.29 (d, J=7.8 Hz, 1H), 7.25 (s, 1H), 7.20 (d, J=7.8 Hz, 1H), 7.13 (d, J=7.8 Hz, 2H), 7.05 (d, J=7.8 Hz, 2H), 4.29 (dd, J=7.3, 4.7 Hz, 1H), 4.26 (s, 2H), 3.39 (dddd, J=10.4, 10.4, 7.8, 7.8 Hz, 1H), 3.29 (dddd, J=10.9, 10.9, 7.8, 7.8 Hz, 1H), 2.99 (dd, J=16.1, 7.3 Hz, 1H), 2.75 (dddd, J=7.3, 7.3, 3.6, 3.6 Hz, 1H), 2.66 (dd, J=16.1, 4.7 Hz, 1H), 2.52-2.46 (m, 2H), 2.32 (s, 3H), 2.26-2.14 (m, 2H), 0.92-0.84 (m, 4H). LRMS m/z (APCI$^+$) 427 (M+1).

EXAMPLE 94

3-[3-(3-Cyclopropylaminomethyl-phenyl)-cyclobutyl]-4-(4-isopropyl-phenyl)-2,4,5,7-tetrahydro-pyrazolo[3,4-b]pyridin-6-one The title compound was prepared in a manner analogous to that described in Example 88 using appropriate starting materials.

500 MHz $^1$H NMR (CD$_3$OD) d 7.37 (dd, J=7.8, 7.8 Hz, 1H), 7.30 (d, J=7.8 Hz, 1H), 7.27 (s, 1H), 7.20 (d, J=8.9 Hz, 1H), 7.19 (d, J=8.3 Hz, 2H), 7.08 (d, J=8.3 Hz, 2H), 4.30 (dd, J=7.3, 4.7 Hz, 1H), 4.27 (s, 2H), 3.39 (dddd, J=10.4, 10.4, 7.8, 7.8 Hz, 1H), 3.28 (dddd, J=J=10.4, 10.4, 7.8, 7.8 Hz, 1H), 3.00 (dd, J=16.1, 7.3 Hz, 1H), 2.89 (ddddd, J=7.3, 7.3, 7.3, 7.3, 7.3, 7.3 Hz, 1H), 2.75 (dddd, J=7.3, 7.3, 3.6, 3.6 Hz, 1H), 2.67 (dd, J=16.1, 5.2 Hz, 1H), 2.53-2.46 (m, 2H), 2.22 (dddd, 10.9, 10.9, 10.9 Hz, 1H), 2.18 (ddd, J=10.4, 10.4, 10.4 Hz, 1H), 1.24 (d, J=7.0 Hz, 6H), 0.94-0.84 (m, 4H). LRMS m/z (APCI$^+$) 455 (M+1).

EXAMPLE 95

4-(3-Chloro-4-fluoro-phenyl)-3-[3-(3-cyclopropylaminomethyl-phenyl)-cyclobutyl]-2,4,5,7-tetrahydro-pyrazolo[3,4-b]pyridin-6-one The title compound was prepared in a manner analogous to that described in Example 88 using appropriate starting materials.

500 MHz $^1$H NMR (CD$_3$OD) 7.39 (dd, J=7.3, 7.3 Hz, 1H), 7.30 (d, J=7.8 Hz, 1H), 7.28-7.24 (m, 3H), 7.20 (dd, J=8.8,8.8 Hz, 1H), 7.13 (ddd, J=8.3, 4.2, 2.1 Hz, 1H), 4.36 (dd, J=6.7, 4.7 Hz, 1H), 4.27 (s, 2H), 3.45 (dddd, J=8.8, 8.8, 8.8, 8.8 Hz, 1H), 3.33 (m, masked under CD$_3$OD, 1H), 3.03 (dd, 16.1, 7.3 Hz, 1H), 2.78-2.74 (m, 1H), 2.65 (dd, J=16.1, 4.2 Hz, 1H), 2.59-2.48 (m, 2H), 2.24-2.17 (m, 2H), 0.94-0.86 (m, 4H). LRMS m/z (APCI$^+$) 465 (M+1).

Biological Methodologies

GSK-3 Inhibition

The specific activity of a compound, stereoisomer, or prodrug of formula (I) in inhibiting GSK-3 can be determined in both cell-free and cell-based assays, both of which have been previously described in the relevant art. See, for example, U.S. Pat. Nos. 6,417,185 and 6,489,344, the disclosures of which are incorporated herein by reference in their entirety.

A cell-free assay can be generally carried out by incubating GSK-3 with a peptide substrate, radiolabeled ATP (e.g., for example, γ$^{33}$P- or γ$^{32}$P-ATP, both of which are available from Amersham; Arlington Heights, Ill.), magnesium ions, and the compound to be assayed. The mixture is incubated for a period of time to allow incorporation of radiolabeled phosphate into the peptide substrate by GSK-3 activity. The reaction mixture is then washed to remove unreacted radiolabeled ATP, typically after first transferring all or a portion of the enzyme reaction mixture to a well that contains a uniform amount of a ligand capable of binding to the peptide substrate. The amount of γ$^{33}$P or γ$^2$P remaining in each well after washing is then quantified to determine the amount of radiolabeled phosphate incorporated into the peptide substrate. Inhibition is observed as a reduction, relative to a control, in the incorporation of radiolabeled phosphate into the peptide substrate. An example of a suitable GSK-3 peptide substrate for an assay is the SGSG-linked CREB peptide sequence, described in Wang, et al., Anal. Biochem., 220, 397402 (1994). Purified GSK-3 for an assay may, for example, be obtained from cells transfected with a human GSK-3β expression plasmid as described in, for example, Stambolic, et al., Current Biology, 6, 1664-1668 (1996).

Another example of a GSK-3 assay, similar to the one described hereinabove, is as follows: enzyme activities are assayed as the incorporation of $^{33}$P from gamma phosphate of $^{33}$P-ATP (Amersham; Arlington Heights, Ill.; catalog #AH-9968) into biotinylated peptide substrate PKTP-KKAKKL. Reactions are carried out in a buffer containing 50 mM Tris-HCl, pH 8.0; 10 mM MgCl$_2$, 0.1 mM Na$_3$VO$_4$, and 1 mM DTT. The final concentration of ATP is 0.5 µM (final specific radioactivity of 4 µCi/mmol), and the final concentration of substrate is 0.75 µM. Reactions, initiated by the addition of enzyme, are carried out at room temperature for about 60 min. Reactions are stopped by addition of 0.6 volume of buffer containing (final concentrations): 2.5 mM EDTA, 0.05% Triton-X 100, 100 µM ATP, and 1.25 mg/ml streptavidin-coated SPA beads (Amersham; Arlington Heights, Ill.; catalog #RPNQ0007). Radioactivity associated with the beads is then quantified by scintillation counting.

A generally preferred GSK-3 testing assay, similar to the one described hereinabove, is as follows: enzyme activities are assayed as the incorporation of $^{33}$P from the gamma phosphate of $^{33}$P-ATP (Amersham; Arlington Heights, Ill.; catalog #AH-9968) into biotinylated peptide substrate Biotin-SRHSSPHQpSEDEEE-OH (AnaSpec Inc., San Jose, Calif.). The reactions are carried out in a buffer containing 8 mM MOPS; 10 mM Mg(OAc)$_2$, 0.2 mM EDTA (pH 7.0), and 1 mM DTT. The final concentration of ATP is 2.0 µM (final specific radioactivity of 4 µCi/nmol), and the final concentration of substrate is 1.0 µM. The reactions, initiated by the addition of enzyme, are carried out at room temperature for about 75 minutes. The reactions are stopped by addition of 0.6 volume of buffer containing (final concentrations): 0.05 mM EDTA, 0.1% Triton-X 100, 100 µM ATP, and 2.5 mg/ml streptavidin-coated SPA beads. Radioactivity associated with the beads is then quantified by standard scintillation counting.

The compounds of formula (I) generally exhibit inhibitory activity, expressed as IC$_{50}$'s, against GSK-3 that are <10,000 nM. Generally preferred compounds have IC$_{50}$'s <200 nM. For example, the compound 3-cyclobutyl-4-(2-methoxypyrimidin-4-yl)-2,4,5,7-tetrahydro-pyrazolo[3,4-b]pyridin-6-one has an IC$_{50}$ of 6.5 nM.

What is claimed is:

1. A compound of formula (I)

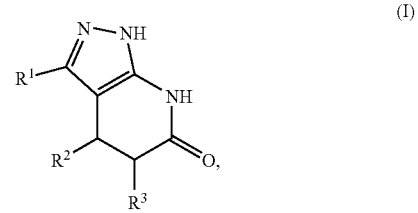

or a stereoisomer thereof, or a pharmaceutically acceptable salt of the compound or stereoisomer, wherein:

R$^1$ and R$^2$ are, independently, hydrogen; —(C$_1$-C$_8$)alkyl; —(C$_1$-C$_8$)alkoxy; —(C$_3$-C$_{11}$)cycloalkyl; heterocycloalkyl; aryl; or heteroaryl; and R$^3$ is hydrogen; —(C$_1$-C$_8$)alkyl; —(C$_1$-C$_8$)alkoxy; or —(C$_3$-C$_{11}$)cycloalkyl;

wherein each R$^1$, R$^2$, and R$^3$ is optionally, and independently, substituted with from one to six of: (A) halogen; (B) aryl, optionally substituted with from one to three of: (i) —OH; (ii) —CN; (iii) halogen; (iv) heteroaryl; (v) —CH$_2$OR$^4$; or (vi) —CH$_2$NR$^4$R$^5$; (C) heteroaryl; (D) —NO$_2$; (E) —CN; (F) —(C$_1$-C$_8$)alkyl, optionally substituted with from one to three halogen atoms; (G) —(C$_1$-C$_8$)thioalkoxy; (H) —NR$^4$R$^5$; (I) —NR$^4$C(=O)R$^5$; (J) —NR$^4$C(=O)NR$^4$R$^5$; (K) —NR$^4$(SO$_2$)R$^5$; (L) —NR$^4$(SO$_2$)NR$^4$R$^5$; (M) —OR$^4$; (N) —OC(=O)R$^4$; (O) —OC(=O)OR$^4$; (P) —C(=O)OR$^4$; (Q) —C(=O) R$^4$; (R) —C(=O)NR$^4$R$^5$; (S) —OC(=O)NR$^4$R$^5$; (T) —OC(=O)SR$^4$; (U) —SR$^4$; (V) —S(=O)R$^4$; (W) —SO$_2$R$^4$; or (X) —SO$_2$R$^4$R$^5$; wherein:

R$^4$ and R$^5$ are, independently, hydrogen; aryl, optionally substituted with from one to three of: halogen; —OH; —(C$_1$-C$_8$)alkyl, optionally substituted with aryl; or —(C$_3$-C$_{11}$)cycloalkyl;

provided that when R¹ is

wherein X is hydrogen, —CH₃, —OCH₃, Cl, Br, or —NO₂, and R² is

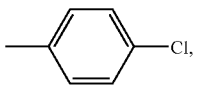

then R³ is not hydrogen.

2. A compound of claim 1, wherein:
R¹ is —(C₁-C₅)alkyl or —(C₃-C₆)cycloalkyl;
R² is hydrogen; —(C₁-C₈)alkyl; —(C₁-C₈)alkoxy; —(C₃-C₉)cycloalkyl; heterocycloalkyl; aryl; or heteroaryl; and
R³ is hydrogen; —(C₁-C₃)alkyl; —(C₁-C₆)alkoxy; or —(C₃-C₆)cycloalkyl;
wherein each R¹, R², and R³ is optionally, and independently, substituted with from one to six of: (A) halogen; (B) aryl, optionally substituted with from one to three of: (i) —OH; (ii) —CN; (iii) halogen; (iv) heteroaryl; (v) —CH₂OR⁴; or (vi) —CH₂NR⁴R⁵; (C) heteroaryl; (D) —NO₂; (E) —CN; (F) —(C₁-C₈)alkyl, optionally substituted with from one to three fluorine atoms; (G) —(C₁-C₈)thioalkoxy; (H) —NR⁴R⁵; (I) —NR⁴C(=O)R⁵; (J) —NR⁴C(=O)NR⁴R⁵; (K) —NR⁴(SO₂)R⁵; (L) —NR⁴(SO₂)NR⁴R⁵; (M) —OR⁴; (N) —OC(=O)R⁴; (O) —OC(=O)OR⁴; (P) —C(=O)OR⁴; (Q) —C(=O)R⁴; (R) —C(=O)NR⁴R⁵; (S) —OC(=O)NR⁴R⁵; (T) —OC(=O)SR⁴; (U) —SR⁴; (V) —S(=O)R⁴; (W) —SO₂R⁴; or (X) —SO₂R⁴R⁵.

3. A compound of claim 1, wherein:
R¹ is —(C₁-C₅)alkyl or —(C₃-C₆)cycloalkyl;
R² is hydrogen; —(C₁-C₈)alkyl; —(C₁-C₈)alkoxy; —(C₃-C₉)cycloalkyl; heterocycloalkyl; aryl; or heteroaryl; and
R³ is hydrogen;
wherein each R¹ or R² is optionally, and independently, substituted with from one to six of: (A) Cl or Fl; (B) aryl, optionally substituted with from one to three of: (i) —OH; (ii) —CN; (iii) halogen; (iv) heteroaryl; (v) —CH₂OR⁴; (vi) or (vii) —CH₂NR⁴R⁵; (C) heteroaryl; (E) —CN; (F) —CF₃; (G) —(C₁-C₈)thioalkoxy; (H) —NR⁴R⁵; (I) —NR⁴C(=O)R⁵; (J) —NR⁴C(=O)NR⁴R⁵; (K) —NR⁴(SO₂)R⁵; (L) —NR⁴(SO₂)NR⁴R⁵; (M) —OR⁴; (O) —OC(=O)OR⁴; (N) —OC(=O)R⁴; (P) —C(=O)OR⁴; (Q) —C(=O)R⁴; (R) —C(=O)NR⁴R⁵; (S) —OC(=O)NR⁴R⁵; (T) —OC(=O)SR⁴; (W) —SO₂R⁴; or (X) —SO₂R⁴R⁵.

4. A compound of claim 1 selected from the group consisting of:
benzylcarbamic acid-3-(6-oxo-4-phenyl-4,5,6,7-tetrahydro-2H-pyrazolo[3,4-b]pyridin-3-yl)-cyclobutyl ester;
2-(3,4-dichloro-phenyl)-N-[3-(6-oxo-4-phenyl-4,5,6,7-tetrahydro-2H-pyrazolo[3,4-b]pyridin-3-yl)-cyclobutyl]-acetamide;
3-cyclobutyl-4-cyclohex-3-enyl-2,4,5,7-tetrahydro-pyrazolo[3,4-b]pyridin-6-one;
3-cyclobutyl-4-(2-dimethylamino-phenyl)-2,4,5,7-tetrahydro-pyrazolo[3,4-b]pyridin-6-one;
3-cyclobutyl-4-(4-dimethylamino-phenyl)-2,4,5,7-tetrahydro-pyrazolo[3,4-b]pyridin-6-one;
3-cyclobutyl-4-(2-dimethylamino-4-fluoro-phenyl)-2,4,5,7-tetrahydro-pyrazolo[3,4-b]pyridin-6-one;
3-cyclobutyl-4-(4-dimethylamino-2-fluoro-phenyl)-2,4,5,7-tetrahydro-pyrazolo[3,4-b]pyridin-6-one;
3-cyclobutyl-4-pyridin-2-yl-2,4,5,7-tetrahydro-pyrazolo[3,4-b]pyridin-6-one;
3-cyclobutyl-4-pyridin-3-yl-2,4,5,7-tetrahydro-pyrazolo[3,4-b]pyridin-6-one;
3-cyclobutyl-4-pyridin-4-yl-2,4,5,7-tetrahydro-pyrazolo[3,4-b]pyridin-6-one;
3-cyclobutyl-4-(2-methoxy-pyrimidin-4-yl)-2,3,4,7-tetrahydro-pyrazolo[3,4-b]pyridin-6-one;
3-cyclobutyl-4-(3,4-difluoro-phenyl)-2,4,5,7-tetrahydro-pyrazolo[3,4-b]pyridin-6-one;
3-cyclobutyl-4-(2,4-dimethoxy-pyrimidin-5-yl)-2,4,5,7-tetrahydro-pyrazolo[3,4-b]pyridin-6-one;
3-cyclobutyl-4-(2,4-dimethyl-phenyl)-2,4,5,7-tetrahydro-pyrazolo[3,4-b]pyridin-6-one;
3-cyclobutyl-4-(3,4-dimethyl-phenyl)-2,4,5,7-tetrahydro-pyrazolo[3,4-b]pyridin-6-one;
3-cyclobutyl-4-(4-imidazol-1-yl-phenyl)-2,4,5,7-tetrahydro-pyrazolo[3,4-b]pyridin-6-one;
3-cyclobutyl-4-(4-isopropyl-phenyl)-2,4,5,7-tetrahydro-pyrazolo[3,4-b]pyridin-6-one;
4-benzyl-3-cyclobutyl-2,4,5,7-tetrahydro-pyrazolo[3,4-b]pyridin-6-one;
4-benzyloxymethyl-3-cyclobutyl-2,4,5,7-tetrahydro-pyrazolo[3,4-b]pyridin-6-one;
4-cyclohex-3-enyl-3-[3-(3-cyclopropylaminomethyl-phenyl)-cyclobutyl]-2,4,5,7-tetrahydro-pyrazolo[3,4-b]pyridin-6-one;
2-(2-chloro-phenoxy)-N-[3-(6-oxo-4-trifluoromethyl-4,5,6,7-tetrahydro-2H-pyrazolo[3,4-b]pyridin-3-yl)-cyclobutyl]-acetamide;
3-[3-(3-cyclopropylaminomethyl-phenyl)-cyclobutyl]-4-ethyl-2,4,5,7-tetrahydro-pyrazolo[3,4-b]pyridin-6-one;
3-[3-(3-cyclopropylaminomethyl-phenyl)-cyclobutyl]-4-isopropyl-2,4,5,7-tetrahydro-pyrazolo[3,4-b]pyridin-6-one;
3-[3-(3-cyclopropylaminomethyl-phenyl)-cyclobutyl]-4-p-tolyl-2,4,5,7-tetrahydro-pyrazolo[3,4-b]pyridin-6-one;
3-(3-{3-[(cyclopropylmethyl-amino)-methyl]-phenyl}-cyclobutyl)-4-(2,4,5-trifluoro-phenyl)-2,4,5,7-tetrahydro-pyrazolo[3,4-b]pyridin-6-one;
3-[3-(3-aminomethyl-phenyl)-cyclobutyl]-4-trifluoromethyl-2,4,5,7-tetrahydro-pyrazolo[3,4-b]pyridin-6-one;
3-[3-(3-cyclopropylaminomethyl-phenyl)-cyclobutyl]-4-p-tolyl-2,4,5,7-tetrahydro-pyrazolo[3,4-b]pyridin-6-one;
3-[3-(3-cyclopropylaminomethyl-phenyl)-cyclobutyl]-4-(4-isopropyl-phenyl)-2,4,5,7-tetrahydro-pyrazolo[3,4-b]pyridin-6-one;
3-[3-(3-hydroxymethyl-phenyl)-cyclobutyl]-2,4,5,7-tetrahydro-pyrazolo[3,4-b]pyridin-6-one;
3-[3-(3-hydroxymethyl-phenyl)-cyclobutyl]-4-trifluoromethyl-2,4,5,7-tetrahydro-pyrazolo[3,4-b]pyridin-6-one;
3-[3-(3-hydroxymethyl-phenyl)-cyclobutyl]-4-(2,4,5-trifluoro-phenyl)-2,4,5,7-tetrahydro-pyrazolo[3,4-b]pyridin-6-one;
3-[3-(6-oxo-4-trifluoromethyl-4,5,6,7-tetrahydro-2H-pyrazolo[3,4-b]pyridin-3-yl)-cyclobutyl]-benzonitrile;

4-(3-chloro-4-fluoro-phenyl)-3-cyclobutyl-2,4,5,7-tetrahydro-pyrazolo[3,4-b]pyridin-6-one;

4-(3-chloro-4-fluoro-phenyl)-3-[3-(3-cyclopropylaminomethyl-phenyl)-cyclobutyl]-2,4,5,7-tetrahydro-pyrazolo[3,4-b]pyridin-6-one; and 4-(3-cyclobutyl-6-oxo-4,5,6,7-tetrahydro-2H-pyrazolo[3,4-b]pyridin-4-yl)-benzoic acid methyl ester;

or a stereoisomer therof, or a pharmaceutically acceptable salt of the compound or streoisomer.

5. A pharmaceutical composition comprising:
(a) a therapeutically effect amount of compound of claim 1,
or a stereoisomer thereof, or
a pharmaceutically acceptable salt or stereoisomer, and
(b) a pharmaceutically acceptable carrier, vehicle, or diluent.

6. A pharmaceutical composition comprising:
(a) a therapeutically effect amount of a compound of claim 1,
or a stereoisomer thereof,
or a pharmaceutically acceptable salt or stereoisomer, and
(b) an amount of one or more of: (i) an anti-angiogenesis agent, (ii) a signal transduction inhibitor, (iii) an anti-proliferative agent, (iv) an NK-1 receptor antagonist, (v) a 5HT$_{1D}$ receptor antagonist, (vi) a selective serotonin reuptake inhibitor, (vii) an anti-psychotic agent, (viii) an acetylcholinesterase inhibitor, (ix) a neuroprotectant, (x) tissue plasminogen activator, (xi) neutrophil inhibitory factor, or (xii) a potassium channel modulator; and
(c) a pharmaceutically acceptable carrier, vehicle, or diluent.

7. A composition of claim 6, wherein: (i) said anti-angiogenesis agent is celecoxib, valdecoxib, or rofecoxib; (ii) said signal transduction inhibitor is an epidermal growth factor receptor response inhibitor, a vascular endothelial growth factor inhibitor, or an erbB2 receptor inhibitor; (iii) said selective serotonin reuptake inhibitor is fluoxetine, paroxetine, sertraline, fluvoxamine, venlafaxine, nefazodone, or bupropion; (iv) said anti-psychotic agent is ziprasidone, olanzapine, risperidone, sonepiprazole, or gepirone; (v) said acetylcholinesterase inhibitor is donepezil, rivastigmine, metrifonate, physostigmine, or tacrine; and (vi) said neuroprotectant is an NMDA receptor antagonist.

* * * * *